United States Patent [19]

Kreighbaum et al.

[11] 4,234,595

[45] Nov. 18, 1980

[54] 3-INDOLYL-TERTIARY BUTYLAMINOPROPANOLS

[75] Inventors: William E. Kreighbaum; William T. Comer, both of Evansville, Ind.

[73] Assignee: Mead Johnson & Company, Evansville, Ind.

[21] Appl. No.: 7,525

[22] Filed: Jan. 29, 1979

Related U.S. Application Data

[63] Continuation-in-part of Ser. No. 815,138, Jul. 13, 1977, abandoned.

[51] Int. Cl.[3] .................. A61K 31/40; C07D 209/12; C07D 209/14
[52] U.S. Cl. .................. 424/274; 260/326.12 R; 260/326.15 B; 260/326.15
[58] Field of Search .................. 260/326.15, 326.12 R, 260/326 BB; 424/274

[56] References Cited

U.S. PATENT DOCUMENTS

| | | |
|---|---|---|
| 2,908,691 | 10/1959 | Robinson .................. 260/319 |
| 3,328,417 | 6/1967 | McLoughlin et al. .......... 260/326.15 |
| 3,852,291 | 12/1974 | Augstein et al. .................. 544/322 |

FOREIGN PATENT DOCUMENTS 834751  2/1970  Canada .

OTHER PUBLICATIONS

Van Arman et al. J. Pharm. & Exp. Therap. 133 Jul. 1961 pp. 90–97.
Jackman et al. J. Pharm. Pharmacol, 17, pp. 742–746 (1965).

*Primary Examiner*—Donald G. Daus
*Assistant Examiner*—D. B. Springer
*Attorney, Agent, or Firm*—Robert E. Carnahan; Robert H. Uloth

[57] ABSTRACT

1-Phenoxy-3-[(3-indolyl)-tert.-butyl]amino-2-propanols and related 1-aryloxy compounds are antihypertensive agents having vasodilator and adrenergic β-receptor blocking action. Preferred compounds bear an ortho-substituent in the phenoxy group, and most preferably the cyano group.

106 Claims, No Drawings

3-INDOLYL-TERTIARY BUTYLAMINOPROPANOLS

REFERENCE TO RELATED APPLICATION

This application is a continuation-in-part of co-pending application Ser. No. 815,138 filed July 13, 1977, now abandoned.

FIELD OF THE INVENTION

The present invention is concerned with heterocyclic carbon compounds of the indole series having an amino substituent (Class 260/326.15), and with drug, bio-affecting and body-treating processes employing these compounds (Class 424/274).

DESCRIPTION OF THE PRIOR ART

I. A substantial body of prior art has developed during the last ten years involving compounds of the 3-aryloxy-2-hydroxypropylamine series which have β-adrenergic receptor blocking activity and are useful in the treatment of cardiovascular diseases. These structures are typified by the substance 1-isopropylamino-3-(1-naphthoxy)-2-propanol which is currently in medical use under the non-proprietary name propranolol. Propranolol and a related group of naphthoxypropanolamines are the subject of U.S. Pat. No. 3,337,628 patented Aug. 22, 1967. A large number of patents have been granted since that time on carbocyclic ethers in which other aromatic rings replace the naphthoxy group of propranolol. Many of these compounds are in the phenoxy series and others are phenoxy compounds with a fused heterocyclic ring.

II. The following patents and publications describe 3-indolylalkylamino compounds.

Robinson, U.S. Pat. No. 2,908,691 patented Oct. 13, 1959 describes a group of 3-indolylalkylamines having an aralkyl substituent attached to the amino nitrogen atom. These substances have utility as hypnotic, antisecretory, and anti-emetic agents. The product of Example 7 thereof has been referred to as SC10049 having bronchodilator and hyperglycemic action (Van Arman, J. Pharmacol. and Exptl. Therap. 133, 90–97 (1961)).

Wasson, et al., U.S. Pat. No. 3,946,009 patented Mar. 23, 1976 discloses a group of pyrazinyloxpropanolamines among which the 3-indolyl-tert.-butyl group is mentioned as an amino substituent. Refer to column 22, line 15. These substances have adrenergic β-receptor blocking properties.

Jackman, G. B., et al., J. Pharm. Pharmacol., 1965 17, 742–746 entitled "Some Tryptamine Derivatives; 1-Aryloxy-3-[(2-indol-3'-ylethyl)amino]propan-2-ols". 3-Indolylethylaminopropanols were conceived of as central nervous system agents of the tranquilizer type. The only compound found to possess any activity had the structural formula shown below. It reflected only a fraction of the CNS activity of chlorpromazine hydrochloride in laboratory tests, and was considered not worthy of detailed biological study.

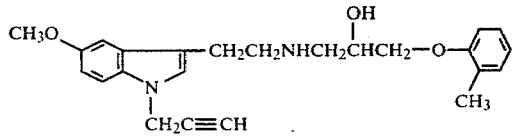

III. The following patent discloses various heterocyclic alkylaminopropanols but no indole compounds are disclosed.

Augstein, et al. U.S. Pat. No. 3,852,291 patented Dec. 3, 1974. Pyrimidinyl alkylamino and imidazolinylalkylamino propanols are described which have adrenergic β-receptor blocking action.

IV. The following patents describe aryloxypropanolamino compounds in which the aryloxy group bears a heterocyclic substituent.

McLoughlin, et al. U.S. Pat. No. 3,328,417 patented June 27, 1967 discloses phenoxypropanolamines in which the phenoxy substituent is further substituted by the 2-indolyl group (Column 2, line 12).

Muchowski, et al. U.S. Pat. No. 3,940,407 patented Feb. 24, 1976 discloses a series of phenoxypropanolamine compounds in which the phenoxy substituent is further substituted by a 1,2,3-thiadiazole substituent.

Seeman, U.S. Pat. No. 3,965,095 patented June 22, 1976 discloses a series of oxindole ethers in which the etherifying group is attached to the phenyl ring and has an esterified aminopropanol configuration. These substances are antiarrhythmic and β-blocking agents.

Troxler, Canadian Pat. No. 834,751 issued Feb. 17, 1970 discloses a series of indole derivatives having a 3-(N-substituted amino)-2-propanoloxy substituent in the 4-position of the indole ring. The compounds are useful in the therapy of coronary disease, angina, cardiac arrhythmia, and hypertension.

Jaeggi, et al., U.S. Pat. No. 3,984,436 patented Oct. 5, 1976 discloses a series of phenoxypropanolamines in which the phenoxy substituent is further substituted by the 1-pyrrolyl group. These compounds are blockers of adrenergic β-receptors.

SUMMARY OF THE INVENTION

The present invention includes the compounds of Formula I and the acid addition salts of these substances

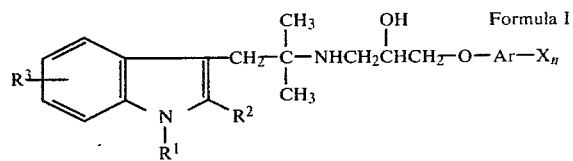

In the foregoing structural formula the symbols $R^1$, $R^2$, $R^3$, Ar, X, and n have the following meanings. One of $R^1$ and $R^2$ is hydrogen and the other is hydrogen or alkyl having 1 to 4 carbon atoms, $R^3$ is hydrogen, halogen, alkyl having 1 to 4 carbon atoms, or alkoxy having 1 to 4 carbon atoms located in the 4-, 5-, 6-, or 7- positions of the indole ring, Ar is selected from the group consisting of phenyl and naphthyl, X refers to 1 or 2 optional Ar-attached substituents which are located in any of the available ring positions and are independently selected from the group consisting of alkyl, alkenyl, alkynyl, alkoxy, alkenoxy, alkynoxy, alkoxyalkyl, alkanoyl, alkenoyl, alkanoyloxy, alkenoyloxy, alkylsulfonyl, alkylsulfinyl, alkylthio, alkanoylamino, alkenoylamino, alkoxycarbonyl, alkenoxycarbonyl, alkoxycarbonylamino, alkoxycarbonylaminoalkyl, cycloalkyl having 3 to 6 ring members and 1 to 3 optional alkyl substituents, cycloalkenyl having 4 to 6 ring members and up to 3 optional alkyl substituents, cycloalkylalkyl having 3 to 6 ring members and up to 3 optional alkyl substituents, cycloalkenylalkyl having 4 to 6 ring members and up to 3 optional alkyl substituents with the additional proviso that each of the foregoing Ar-attached substituents has up to 8 carbon atoms, trifluoromethyl, nitro, amino, hydroxyl, halogen, aminocarbonyl, cyano, cyanoalkyl having from 2 to 4 carbon atoms, aminocarbonylalkyl having 2 to 4 carbon atoms, n is the integer 0, 1, or 2 signifying the number of X groups, or Ar-$X_n$ as a unit refers to 4-indenyl, 6,7-dihydroxy-5,6,7,8-tetrahydro-1-naphthyl, or 5-oxo-5,6,7,8-tetrahydro-1-naphthyl.

When $R^3$ or X is halogen, it is intended to include fluorine, chlorine, bromine, and iodine. Also, when n is 2 and the X substituents are adjacent, those which are sterically incompatible, that is incapable of occupying adjacent positions such as adjacent tertiary alkyl groups, are not intended by the formula.

The compounds of the present invention are unique as antihypertensive agents in that they combine adrenergic $\beta$-blocking and vasodilator activity. They also have utility as anti-anginal agents, anti-stress agents, antiarrhythmic agents, antithrombogenic agents and in the treatment of conditions where it is desirable to reduce the oxygen demand of the heart such as post-myocardial infarct management. Preferred members have a particularly desirable combination of the foregoing actions, and ancillary pharmacological effects, or a lack thereof, which particularly suits them for specific indications from among those listed. Those of Formula I wherein Ar is phenyl, n=1, and X is located in the ortho position are preferred for antihypertensive use. The utility of the compounds of Formula I can be demonstrated in various animal models including antagonism of isoproterenol in the conscious rat treated orally (adrenergic $\beta$-receptor blocking action), the spontaneous hypertensive rat (antihypertensive action), the dog hind limb preparation (vasodilator action), angiotensin-maintained ganglion blocked rat model (vasodilator action), ouabain-induced ventricular tachycardia in the dog (antiarrhythmic action), in the coronary artery occluded dog (antiarrhythmic action), in vitro by measuring platelet aggregation in platelet-rich plasma photometrically following challenge with a thrombogenic agent such as adenosine diphosphate or collagen (antithrombogenic action), and in various other animal and laboratory models.

DETAILED DESCRIPTION OF THE INVENTION

The invention includes compounds having the foregoing structural formula and the acid addition salts thereof. For medical use, the pharmaceutically acceptable acid addition salts are preferred. The pharmaceutically acceptable acid addition salts are those salts in which the anion does not contribute significantly to the toxicity or pharmacological activity of the salt, and as such, they are the pharmacological equivalents of the bases having the foregoing structural formulas. In some instances, the salts have physical properties which make them more desirable for pharmaceutical formulation purposes such as solubility, lack of hygroscopicity, compressibility with respect to tablet formation and compatibility with other ingredients with which the substances may be used for pharmaceutical purposes. Acid addition salts which do not meet the foregoing criteria for pharmaceutical acceptability, for instance as to toxicity, are sometimes useful as intermediates for isolation and purification of the present substances or for other chemical synthetic purposes such as separation of optical isomers. Such salts are also part of the invention.

The acid addition salts are made by reaction of a base of the foregoing structural formula with the acid preferably by contact in solution. They may also be made by metathesis or treatment with an anion exchange resin whereby the anion of one salt of the substance is replaced by another anion under conditions which allows for separation of the undesired species such as by precipitation from solution or extraction into a solvent or elution from or retention on an anion exchange resin. Pharmaceutically acceptable acids for the purposes of salt formation include hydrochloric, hydrobromic, hydroiodic, citric, acetic, benzoic, phosphoric, nitric, mucic, isethionic, methanesulfonic, p-toluenesulfonic, glucosaccharic, palmitic, heptanoic, oxalic, cyclamic, succinic, malic, fumaric, mandelic, malonic, and others.

The compounds of the present invention shown by the foregoing structural formula contain an asymmetric carbon atom in the propanolamine side chain and occur as optically active isomers as well as racemic mixtures thereof. The present invention is intended to include each of the optically active and racemic forms. Some of the substances of the present invention contain an asymmetric carbon atom in the X substituent, and diastereoisomeric pairs of racemates exist. These forms are also included.

Resolution of racemic mixtures to provide the optically active isomers of the foregoing compounds is carried out, for example, by forming a salt with an optically active acid many of which are known to those skilled in the art such as optically active tartaric, mandelic, cholic, O,O-di-p-toluoyl tartaric, and O,O-dibenzoyl tartaric acids, or other acids conventionally employed for this purpose. The claims, therefore, will be understood to embrace the products in the form of the several racemic mixtures as well as in the form of the optically active isomers where appropriate.

The therapeutic processes of this invention comprise systemic administration of an effective, non-toxic amount of a compound of Formula I or a pharmaceutically acceptable acid addition salt thereof to a mammal having a disease state resulting from excessive stimulation of the adrenergic $\beta$-receptors, or to a mammal requiring vasodilation, or to a mammal having hypertension. An effective amount is construed to mean a dose which exerts an adrenergic $\beta$-receptor blocking action, a vasodilator effect, or antihypertensive action in the affected animal without undue toxic side effects. By systemic administration, it is intended to include both oral and parenteral routes. Examples of parenteral administration are intravenous injection or infusion, and intraperitoneal, intramuscular or subcutaneous injection. Rectal administration by ointment or suppository may be employed. Dosage will vary according to the route of administration with from about 0.1 mcg to 100 mg/kg body weight of a compound of Formula I or a pharmaceutically acceptable acid addition salt thereof generally providing the desired therapeutic effect. Acute toxicities measured in the mouse treated orally are within the range of about $ALD_{50}$ 125 mg/kg to >2000 mg/kg of body weight, with non-lethal signs of drug effect such as central nervous system stimulation or depression, mydriasis, or lacrimation appearing at from 1/2 to 1/10 that dose.

The combination of pharmacological properties of the compounds of Procedure 10, 1-[[2-(3-indolyl)-1,1-dimethylethyl]-amino]-3-(2-methylphenoxy)-2-propanol hydrochloride, and Procedure 26, 2-[2-hydroxy-3-[[2-(3-indolyl)-1,1-dimethylethyl]amino]-propoxy]-benzonitrile hydrochloride, indicates that they are particularly desirable for antihypertensive use. They have five-fold the adrenergic β-receptor blocking potency of propranolol shown by oral administration to rats followed by challenge of the animals with isoproterenol administered intravenously (Test Method 349F). The latter is a well known adrenergic β-receptor stimulant which causes an increase in heart rate and a decrease in blood pressure. These effects of isoproterenol are antagonized by adrenergic β-receptor blocking agents, and the relative potency values given above were prepared by regression analysis of log dose-response data for the compounds. For therapeutic use, dosage size and frequency will vary with the subject and the route of administration, with from about 0.2 mg. for intravenous administration up to about 100 mg orally being suitable for man.

The substances of Procedures 10 and 26 are distinguished from other adrenergic β-receptor blocking drugs in that they are effective in lowering the blood pressure in the spontaneously hypertensive rat (Test Method 410C). Although adrenergic β-receptor blocking agents have come into widespread use in human medicine for the treatment of hypertension, their mechanism of action is unknown and their antihypertensive activity cannot be detected by this animal test in most instances. With the present substances in the spontaneously hypertensive rat, a reduction of blood pressure, respectively, of 25 mm. and 44 mm. of Hg occurs at doses of 100 mg/kg of body weight orally with only a minimal reduction in heart rate. This is thought to be indicative of utility in hypertensive indications where other adrenergic β-receptor blocking drugs are inoperative or less desirable.

The substances of Procedures 10 and 26 also cause a reduction in blood pressure when administered intravenously to the anesthetized dog in a dose of 3.33 mg/kg of body weight. They are further distinguished in that they do not depress heart rate or right ventricular contractile force as is the case with many prior adrenergic β-receptor blocking agents. Both a positive inotropic and a positive chronotropic effect are exhibited by the substances, and these effects are apparent even when the animal is first treated with an adrenergic β-receptor blocking agent such as sotalol. Pulmonary artery pressure remains substantially unchanged, while aortic blood flow and total peripheral resistance are decreased, all of the foregoing in the anesthetized dog.

The compounds of Procedures 10 and 26 possess vasodilator activity which may account, in part, for their unique anti-hypertensive action. In the anesthetized ganglion blocked (chlorisondamine chloride) angiotension supported rat (Test Method 432), direct acting vasodilators such as diazoxide exert a reduction in blood pressure. The substances of Procedures 10 and 26 are at least equivalent in potency to diazoxide in this test. The vasodilator action thereof can also be shown in the pump-perfused hind limb of the dog in doses of from 0.03 to 1.0 mg/min. urine volume and a decrease in sodium ion excretion occurs which is typical of vasodilator compounds.

The antithrombogenic action of the substance of Procedure 10 is reflected by its ability to reduce platelet aggregation in vitro in platelet-rich plasma following challange with ADP or collagen. It is comparable in in vitro activity to suloctidil or to papaverine.

A hazard exists in the use of a preponderance of adrenergic β-receptor blocking agents in patients suffering from non-allergic bronchospasm in view of the tendency of these agents to provoke an asthmatic attack or to render the subject refractory to treatment with adrenergic β-receptor stimulants such as isoproterenol which are used in the treatment of acute attacks. The substances of Procedures 10 and 26 lack bronchospastic liability as is demonstrated by the fact that they do not reduce pulmonary ventilatory pressure, and evoke only moderate enhancement of the response of sensitized rats to immunologically induced broncho-constriction at a dose of 0.5 mg/kg of body weight intravenously. In contrast, propranolol at a dose of 0.5 mg/kg of body weight intravenously reduces pulmonary ventilatory pressure and precipitates an acute bronchospastic response in sensitized rats to immunologically-induced broncho-constriction.

For the preparation of pharmaceutical compositions containing the compounds of Formula I in the form of dosage units for oral administration, the compound is mixed with a solid, pulverulent carrier such as lactose, sucrose, sorbitol, mannitol, potato starch, corn starch, amylopectin, cellulose derivatives, or gelatin, as well as with glidents such as magnesium stearate, calcium stearate, polyethylene glycol waxes or the like and pressed into tablets. The tablets may be used uncoated or coated by known techniques to delay disintegration and absorption in the gastrointestinal tract and thereby provide a sustained action over a longer period. When coated tablets were wanted, the above prepared core may be coated with a concentrated solution of sugar, which solution may contain e.g. gum arabic, gelatin, talc, titanium dioxide or the like. Furthermore, the tablets may be coated with a lacquer dissolved in an easily volatile organic solvent or mixture of solvents and if desired, dye may be added to this coating.

In the preparation of soft gelatin capsules consisting of gelatin and e.g. glycerine and the like, the active ingredient is mixed with a vegetable oil and encapsulated in conventional manner. Hard gelatin capsules may contain granules of the active ingredient in combination with a solid, pulverulent carrier such as lactose, saccharose, sorbitol, mannitol, starch (such as e.g. potato starch, corn starch, or amylopectin), cellulose derivatives or gelatin.

Dose units for rectal administration may be prepared in the form of suppositories containing the compound in a mixture with a neutral fat base, or in the form of a gelatin-rectal capsule with a mixture of vegetable oil or paraffin oil.

Liquid preparations suitable for oral administration are suspensions, syrups and elixirs containing from about 0.2% by weight to about 20% by weight of the active ingredient.

A suitable injectible composition comprises an aqueous solution of a water soluble pharmaceutically acceptable acid addition salt adjusted to physiologically acceptable pH.

The compounds of Formula I are prepared by application of known processes to the appropriate starting materials. Representative know methods for the preparation of aryloxypropanolamine compounds are disclosed in the foregoing patents and publications cited above under Description of the Prior Art of which the Troxler Canadian Pat. No. 834,751 and the Jaeggi, et al., U.S. Pat. No. 3,984,436 are illustrative. More specifically, the present invention provides a process for the preparation of the compounds of Formula I according to the following reaction scheme.

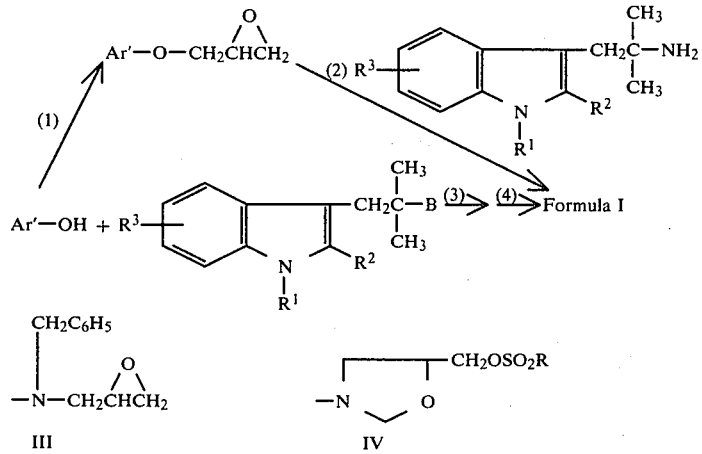

In the foregoing reaction scheme, the symbol Ar' represents the groups Ar, X, and n as they are defined in Formula I, $R^1$, $R^2$, and $R^3$ have the same meaning as in Formula I, and the symbol B is defined by Formulas III and IV in which R is a lower alkyl group of 4 or fewer carbon atoms. The preferred method is according to reactions (1) and (2) in which step (1) involves reacting the appropriately substituted phenolic compound Ar'—OH with epichlorohydrin in the presence of a catalytic quantity of an amine followed by treating with aqueous alkali metal hydroxide, or conducting the reaction in the first instance in an aqueous alkali metal hydroxide reaction medium whence the amine catalyst is not required. There is produced in step (1) an Ar' epoxypropyl ether which is caused to react in step (2) with 2-($R^1$,$R^2$,$R^3$-3-indolyl)-1,1-dimethylethylamine to yield a product of Formula I. Each of reaction steps (1) and (2) takes place facilely in ordinary laboratory or plant equipment under convenient operating conditions.

Heating of epichlorohydrin in substantial molecular excess amount with a phenol Ar'OH containing a drop or two of piperidine as catalyst on a steam bath overnight results in the condensation shown in step (1). Some of the corresponding halohydrin intermediate is also produced and is converted without isolation to the oxirane shown by treatment of the mixture with aqueous alkali metal hydroxide. Alternatively, the Ar'OH phenol and epichlorohydrin can be caused to react in the presence of a sufficient amount of a dilute aqueous alkali metal hydroxide to neutralize the acidic Ar'OH group at room temperature with formation of the desired intermediate

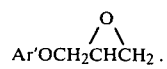

Step (2) is carried out simply by heating the oxirane intermediate produced in step (1) with 2-($R^1$,$R^2$,$R^3$-3-indolyl)-1,1-dimethylethylamine either neat or in the presence of a reaction inert organic solvent. No catalyst or condensation agent is required. Suitable solvents include 95% ethanol but other reaction inert organic liquids in which the reactants are soluble may be employed. These include but are not limited to benzene, toluene, tetrahydrofuran, dibutyl ether, butanol, hexanol, methanol, dimethoxyethane, ethylene glycol, etc. Suitable reaction temperatures are from about 60°–200° C.

An alternate variation of the process for the preparation of compounds of Formula I involves reaction of the Ar'OH starting material as defined above with a reactant of the formula

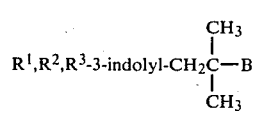

according to reaction (3) of the scheme to yield an intermediate which is transformed to the final product by hydrolysis or hydrogenolysis. The substituent B in the reactant used in step (3) is a group such as shown by III or IV which is reactive with the phenolic hydroxyl group Ar'OH to incorporate into the product an incipient propanolamine side chain.

The reactants for step (3) wherein B has Formula III are prepared by forming the N-benzyl derivative of 2-($R^1$,$R^2$,$R^3$-3-indolyl)-1,1-dimethylethylamine and reacting the latter with epichlorohydrin by adaptation of the method of L. Villa et al., II. Farmaco. Sci., Ed., 24, (3) 349 (1969).

Those reactants wherein B has Formula IV are prepared by reductive alkylation of 2-($R^1$,$R^2$,$R^3$-3-indolyl)-1,1-dimethylethylamine with glyceraldehyde according to known methods, for instance, employing 5% palladium-on-carbon catalyst in an atmosphere of hydrogen with methanol or other suitable non-reactive liquid as solvent. When using an optically active form of glyceraldehyde, an optically active end product of Formula I is obtained. The amino propanediol resulting from the foregoing reductive alkylation reaction is then converted to the desired 2-($R^1$,$R^2$,$R^3$-3-indolyl)-1,1-dimethylethyloxazolidinone reactant wherein B has Formula IV by reaction with formaldehyde employing 37% aqueous formaldehyde in refluxing benzene with continued removal of the water by distillation. Esterification with an alkanesulfonyl chloride of the formula RSO$_2$Cl in which R is a lower alkyl group of 1 to 4 carbon atoms introduces the necessary group which is reactive with Ar'OH.

The intermediate produced by step (3) wherein the B has Formula III is converted in step (4) to a product of Formula I by debenzylation by known means such as catalytic hydrogenation or reaction with sodium in liquid ammonia. The intermediates produced in step (3) wherein B has formula IV are converted to the products of Formula I in step (4) by mild acid hydrolysis. In this instance, care must be taken to avoid decomposition of the reactant since certain R$^1$,R$^2$,R$^3$-3-indolyl substituents are known to be acid sensitive. Aqueous mineral acids of from 0.1 N to 1 N concentration at temperatures of from 20°–100° C. are suitable. The product is recovered as the free base from the hydrolysis mixture by neutralization thereof and collecting the precipitate.

DESCRIPTION OF SPECIFIC EMBODIMENTS 2-(3-Indolyl)-1,1-dimethylethylamine (Chemical Abstracts nomenclature: α,α-dimethyl-1H-indol-3-yl-ethanamine) is prepared by the method of H. R. Snyder, et al., J. Am. Chem. Soc., 69, 3140 (1947) from 3-indolylmethyldimethylamine (gramine) and 2-nitropropane followed by reduction of the resulting 2-(3-indolyl)-1,1-dimethylnitroethane. Various substituted 2-(R$^1$,R$^2$,R$^3$-3-indolyl)-1,1-dimethylethylamines for application to the synthesis of other compounds of Formula I may be prepared by the method of Arvid Ek, et al., J. Amer. Chem. Soc., 76 5583 (1954).

In the following procedures temperatures are expressed in degrees centigrade (°). Melting points are corrected values according to the U.S.P. method where indicated (corr.). The nuclear magnetic resonance (NMR) spectral characteristics refer to chemical shift (δ) expressed as parts per million (ppm) versus tetramethylsilane (TMS) as reference standard. The relative area reported for the various shifts corresponds to the number of hydrogen atoms of the particular functional type in the molecule, and the nature of the shift as to multiplicity is reported as broad singlet (bs), singlet (s), multiplet (m), doublet (d), triplet (t), or quadruplet (q) with coupling constants (J) reported where appropriate. The format is NMR (solvent): δ(relative area, multiplicity, J value). Abbreviations employed are MeOH (methanol), DMSO (dimethylsulfoxide), DMSO-d$_6$ (deuterodimethylsulfoxide), i-PrOH (isopropanol), abs.EtOH (absolute ethanol), EtOAc (ethyl acetate), EtOH (95% ethanol), Et$_2$O (diethyl ether), THF (tetrahydrofuran), MEK (2-butanone), i-PrOAc (isopropyl acetate), i-Pr$_2$O (di-isopropyl ether), AcOH (acetic acid), TLC (thin layer chromatography), d (decomposition). Other abbreviations have conventional established meanings. The infrared (IR) spectral descriptions include only absorption wave numbers (cm$^{-1}$) having functional group identification value. KBr was employed as diluent for all IR spectral determinations. TMS was used as internal reference for the NMR spectral determination. The elemental analyses are reported as percent by weight.

Procedure 1.
4-(METHYLSULFONYL)-m-TOLYLOXYMETHYL OXIRANE

To a mixture of 3-methyl-4-methylsulfonylphenol, 8.1 g. (0.0435 mole), and 20.0 g. (0.216 mole) of epichlorohydrin, there are added two drops of piperidine to serve as condensation catalyst and the mixture is heated at 105°–108° for 18 hrs. The excess epichlorhydrin is then removed by distillation using toluene as a chaser. A solution of 2.1 g. of sodium hydroxide in 50 ml. of water and 70 ml. of dimethoxyethane is then added and the mixture is stirred for 2 hrs. with occasional warming on the steam bath to convert any phenoxychlorohydrin compound to the oxirane. The solvent is then removed by distillation in vacuo and the residue is dissolved in a 1:1 (V/V) mixture of ether and benzene. The solution is dried over anhydrous sodium carbonate and examined by thin layer chromatography for purity of the desired oxirane using a 9:1 mixture of chloroform and a methanol for development (R$_f$=0.8). The solvent is then removed by distillation to yield 10.7 g. of a residue constituting the desired oxirane. Measurement of the infrared absorption spectrum is employed to confirm the substantial absence of hydroxyl containing contaminants. This material is suitable for further reaction in Procedure 3 without further purification.

Procedure 2. 2-CHLOROPHENOXYMETHYL OXIRANE

A solution of 12.9 g. of 2-chlorophenol (0.1 mole) in 125 ml. of water containing 6.5 g. (0.162 mole) of sodium hydroxide, and 18.5 g. (0.2 mole) of epichlorohydrin are stirred together at 25° for 20 hrs. The mixture is then extracted twice with 70 ml. portions of methylene chloride. The extract is dried over anhydrous sodium carbonate and the solvent removed by distillation in vacuo. The residue constitutes the desired oxirane and is suitable for further transformation as is described in Procedure 4.

Procedure 3.
1-[[2-(3-INDOLYL)-1,1-DIMETHYLETHYL]AMINO]-3-[4-(METHYLSULFONYL)-m-TOLYLOXY]-2-PROPANOL HYDROCHLORIDE The oxirane of Procedure 1, 10.7 g. was dissolved in 150 ml. of toluene, 8.2 g. (0.044 mole) of 2-(3-indolyl)-1,1-dimethylethylamine was added and the mixture was refluxed for 18 hrs. The toluene was removed by distillation in vacuo and a portion of the residue was converted to the acetate salt, m.p. 142°–147° C. The structure was confirmed by examination of the infrared absorption and nuclear magnetic resonance spectra. The remainder of the sample was converted to the hydrochloride salt by treatment of an acetonitrile solution thereof with 8 N ethanolic HCl. After recrystallization from CH$_3$CN/MeOH 12.5 g. of product was obtained, m.p. 174.0°–177.0° (corr.).

Anal. Found: C, 59.40; H, 6.90; N, 5.87.

NMR (DMSO-d$_6$): 1.29 (6, s); 2.52 (3, s); 3.12 (3, s); 3.16 (4, m); 4.18 (3, m); 5.95 (1, bs); 7.10 (8, m); 9.00 (2, bs); and 11.12 (1, bs).

IR: 740, 765, 1120, 1290, 1450, 1590, and 3270.

Procedure 4.
1-(2-CHLOROPHENOY)-3-[[2-(3-INDOLYL)-1,1-DIMETHYLETHYL]AMINO]-2-PROPANOL A portion of the oxirane produced in Procedure 2, 7 g. (0.033 mole), was refluxed in solution with 6.3 g. (0.033 mole) of 2-(3-indolyl)-1,1-dimethylethylamine in 70 ml. of ethanol. After 24 hrs. the solvent was removed by distillation in vacuo and the viscous liquid residue was dissolved in 200 ml. of ether, acidified with 8 N ethanolic HCl and the solvents again removed by distillation. Crystallization was induced by adding acetonitrile and rubbing with a glass rod; recystallized from acetonitrile and di-isopropyl ether to yield 4.8 g. of product, m.p. 150.5°–153.5° C. (corr.).

Anal. Found: C, 61.54; H, 6.41; N, 6.94.

NMR (DMSO-$d_6$): 1.28 (6, s); 3.22 (4, m); 4.25 (3, m); 5.96 (1, bs); 7.23 (9, m); 8.84 (2, bs); and 11.12 (1, bs).

IR: 745, 1250, 1455, 1480, 1590, and 2780.

By adaptation of the foregoing procedures, the products listed in the following table were prepared.

PRODUCTS OF FORMULA I
PROCEDURES 5–14

| Procedure No. | ArX | m.p.° (corr.) | Recryst. Solvent | Elemental Analysis | NMR(DMSO-$d_6$) | IR |
|---|---|---|---|---|---|---|
| 5 | 1-naphthyl | 232.0–233.0 hydrochloride | MeOH/CH$_3$CH | C, 70.47<br>H, 7.07<br>N, 6.47 | 1.28 (6,s)<br>3.24 (4,m)<br>4.28 (3,m)<br>6.01 (1,d, 4.4 Hz)<br>7.39 (12,m)<br>8.90 (2,bs)<br>11.00 (1,bs) | 750, 775, 800, 1110, 1270, 1400, 1460, 1580, 2780, |
| 6 | 3-methylphenyl | 165.0–167.0 hydrochloride | MeOH/i-PrOH | C 67.76<br>H, 7.62<br>N, 7.05 | 1.30 (6,s)<br>2.28 (3,s)<br>3.18 (4,m)<br>4.13 (3,m)<br>5.93 (1,bs)<br>7.10 (9,m)<br>8.72 (1,bs)<br>9.12 (1,bs)<br>11.00 (1,bs) | 745, 770, 1160, 1260, 1450, 1490, 1580, 1600, 2780, |
| 7 | 3-chlorophenyl | 197.0–198.0 hydrochloride | MeOH/abs.EtOH | C, 61.34<br>H, 6.36<br>N, 6.75<br>Ch, 17.14 | 1.30 (6,s)<br>3.20 (4,m)<br>4.17 (3,m)<br>6.03 (1,d, 5.0 Hz)<br>7.20 (9,m)<br>8.86 (1,bs)<br>9.30 (1,bs) | 750, 770, 1110, 1230, 1275, 1475, 1580, 1590, 2800, 3340 |
| 8 | 2-ethoxyphenyl | 173.0–175.0 hydrochloride | MeOH/i-PrOH | C, 65.86<br>H, 7.51<br>N, 6.63 | 1.30 (6,s)<br>1.32 (3,t, 7.0 Hz)<br>3.29 (4,m)<br>4.11 (5,m)<br>5.99 (1,bs)<br>7.22 (9,m)<br>8.90 (1,bs)<br>9.31 (1,bs) | 740, 755, 1130, 1215, 1260, 1510, 1580, 1590, 2800, |
| 9 | 2-acetylphenyl | 161.0–163.0 hydrochloride | CH$_3$CN | C, 65.73<br>C, 65.59<br>H, 7.10<br>H, 6.94<br>N, 7.05<br>N, 7.03 | 1.30 (6,s)<br>2.65 (3,s)<br>3.20 (4,m)<br>4.30 (3,m)<br>6.04 (1,bs)<br>7.41 (9,m)<br>8.86 (1,bs) | 745, 755, 1240, 1450, 1485, 1590, 1665, 2780 |
| 10* | 2-methylphenyl | 173.0–174.5 hydrochloride | MeOH/EtOAc | C, 68.09<br>H, 7.77<br>N, 7.16 | 1.30 (6,s)<br>2.20 (3,s)<br>3.28 (4,m)<br>4.15 (3,m)<br>6.02 (1,d, 4.2 Hz)<br>7.22 (9,m)<br>9.15 (2,bs)<br>11.30 (1,bs) | 750, 1170, 1250, 1460, 1500, 2800, 3300 |
| 11 | 2,6-dimethylphenyl | 221.5–224.5 hydrochloride | | C, 67.85<br>H, 7.63<br>N, 6.73 | 1.32 (6,s)<br>2.28 (6,s)<br>3.27 (4,m)<br>3.84 (2,d 5.9 Hz)<br>4.35 (1,m)<br>7.30 (8,m)<br>8.80 (1,bs)<br>9.45 (1,bs)<br>11.20 (1,bs) | 750, 770, 1200, 1260, 1460, 1480, 1590, 1620, 2980, |
| 12 | (4-methylsulfonyl)-phenyl | 217.0–220.0 hydrochloride | MeOH/abs.EtOH | C, 58.32<br>H, 6.62<br>N, 6.90 | 1.30 (6,s)<br>3.16 (3,s)<br>3.35 (4,m)<br>4.26 (3,m)<br>6.07 (1,bs)<br>7.0–8.0 (9,m)<br>8.85 (1,bs)<br>9.25 (1,bs) | 760, 780, 1155, 1300, 1510, 1600, 2800 |
| 13 | 4-acetyl-2-cyanomethyl | 198–199 (dec.) oxalate hemihydrate | | C, 65.66<br>H, 6.30<br>N, 8.96 | 1.19 (6,s)<br>2.54 (3,s)<br>3.02 (4,m) | 750, 1270, 1310, 1500, 1600, 1670, 2980, 3400 |

-continued

PRODUCTS OF FORMULA I
PROCEDURES 5-14

| Procedure No. | ArX | m.p.° (corr.) | Recryst. Solvent | Elemental Analysis | NMR(DMSO-d$_6$) | IR |
|---|---|---|---|---|---|---|
| 14 | 2-(methylsulfonyl)-phenyl | 175.0–179.0 hydrochloride hemihydrate | MeOH/i-Pr$_2$O | C, 57.23 C, 57.37 H, 6.91 H, 6.61 N, 5.90 N, 5.94 | 3.98 (2,s) 4.20 (3,m) 6.60 (3,bs) 7.22 (6,m) 8.00 (2,m) 11.04 (1,bs) 1.39 (6,s) 3.60 (3,s) 3.62 (4,m) 4.42 (3,m) 6.22 (1,m) 7.42 (9,m) 9.00 (1,bs) 9.51 (1,bs) | 750, 1130, 1150, 1300, 1450, 1485, 1590, 1625 |

*Procedure 10 involved reaction of the 2-(3-indolyl)-1,1-dimethylethylamine and the oxirane intermediate at 140° for ½ hour with no solvent or diluent.

TABLETS

The following ingredients are blended in the proportions by weight indicated according to conventional pharmaceutical techniques to provide a tablet base.

| Ingredient | Amount |
|---|---|
| Lactose | 79 |
| Corn starch | 10 |
| Talcum | 6 |
| Tragacanth | 4 |
| Magnesium stearate | 1 |

This tablet base is blended with sufficient 1-[[2-(3-indolyl)-1,1-dimethylethyl]amino]-3-(2-methylphenoxy)-2-propanol hydrochloride (Procedure 10) to provide tablets containing 10, 20, 40, 80, 160 and 320 mg. of active ingredient, and compressed in a conventional tablet press.

DRY FILLED CAPSULES

The following ingredients are blended in a conventional manner in the proportion by weight indicated.

| Ingredient | Amount |
|---|---|
| Lactose, U.S.P. | 50 |
| Starch | 5 |
| Magnesium stearate | 2 |

Sufficient 1-[[2-(3-indolyl)-1,1-dimethylethyl]amino]-3-(2-methylphenoxy)-2-propanol hydrochloride (Procedure 10) is added to the blend to provide capsules containing 10, 20, 40, 80, 160 and 320 mg. of active ingredient which is filled into hard gelatin capsules of a suitable size.

SOLUTION

A solution of 1-[[2-(3-indolyl)-1,1-dimethylethyl]amino]-3-(2-methylphenoxy)-2-propanol hydrochloride (Procedure 10) is prepared from the following ingredients.

| Ingredient | Amount |
|---|---|
| Active ingredient | 20 g. |
| Sucrose, U.S.P. | 400 g. |
| Sorbitol, U.S.P. | 100 g. |
| Bentonite | 20 g. |
| Flavors, q.s. | |
| Water, q.s. to make 1 liter | |

Each milliliter of the solution contains approximately 20 mg. of the active ingredient.

By application of the methods of Procedures 1 or 2 to the appropriate phenol, or by other conventional methods, the following oxiranes are prepared and then converted to products of Formula I by reaction with 2-(3-indolyl)-1,1-dimethylethylamine according to Procedures 3 or 4.

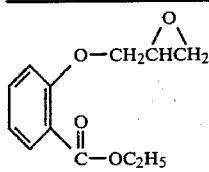

Procedure 15

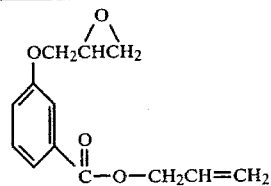

Procedure 16

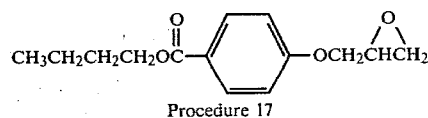

Procedure 17

-continued
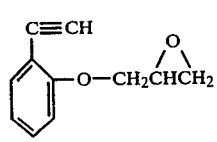
Procedure 18
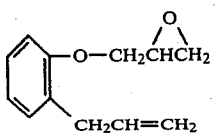
Procedure 19*
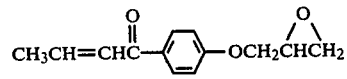
Procedure 20
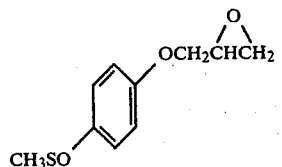
Procedure 21
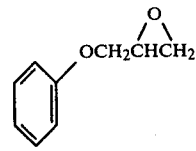
Procedure 22*
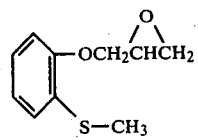
Procedure 23*
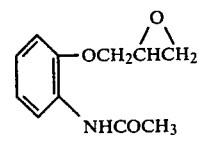
Procedure 24
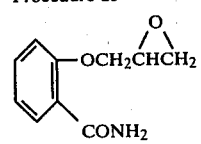
Procedure 25*
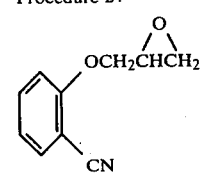
Procedure 26*
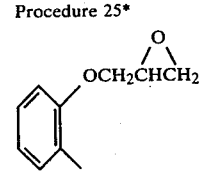
Procedure 27
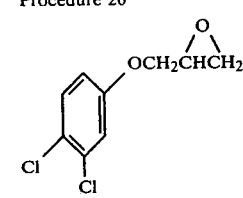
Procedure 28
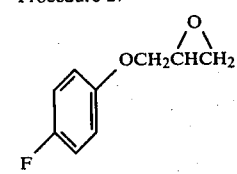
Procedure 29
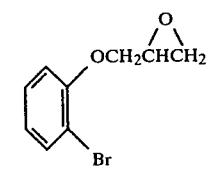
Procedure 30
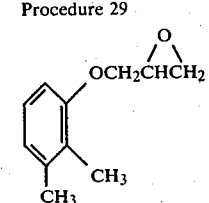
Procedure 31*
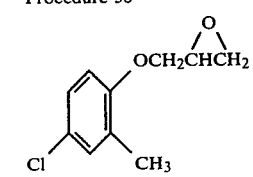
Procedure 32*
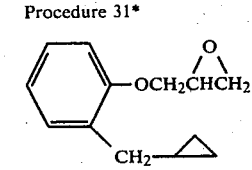
Procedure 33
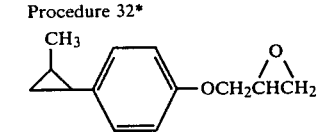
Procedure 34
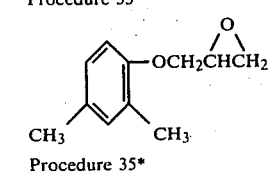
Procedure 35*

-continued
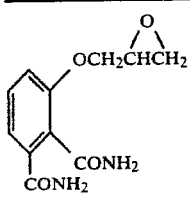
Procedure 36
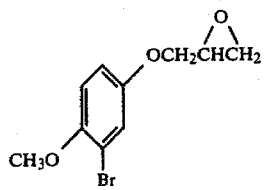
Procedure 37
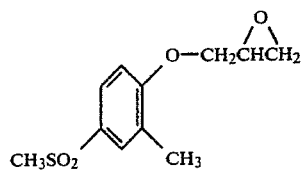
Procedure 38*
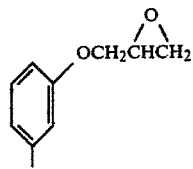
Procedure 39
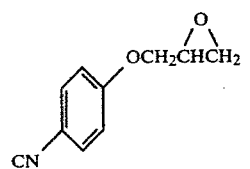
Procedure 40
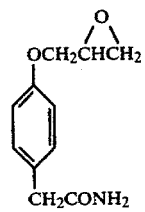
Procedure 41
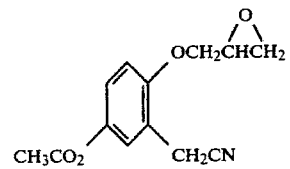
Procedure 42
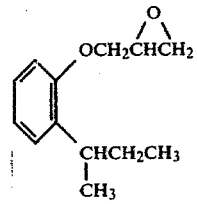
Procedure 43*
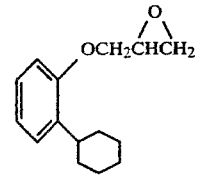
Procedure 44*
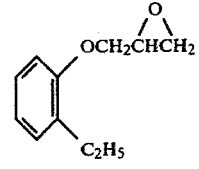
Procedure 45*
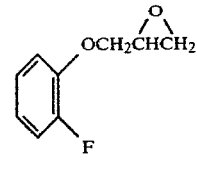
Procedure 46*
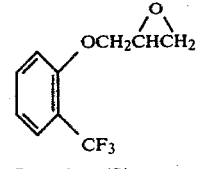
Procedure 47*
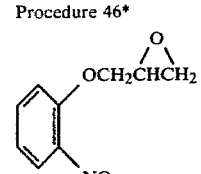
Procedure 48*
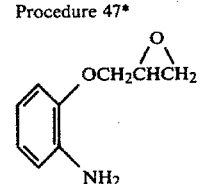
Procedure 49*
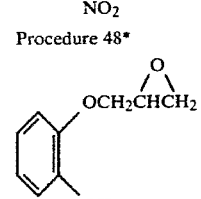
Procedure 50
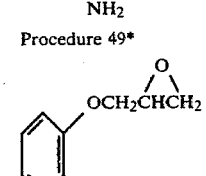
Procedure 51

-continued
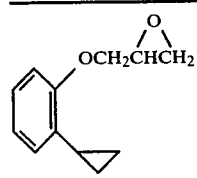
Procedure 52
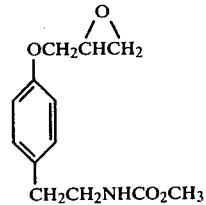
Procedure 54
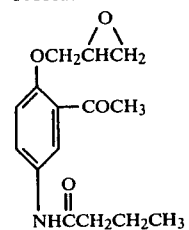
Procedure 56
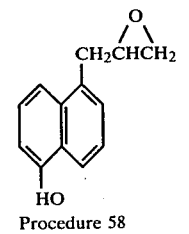
Procedure 58
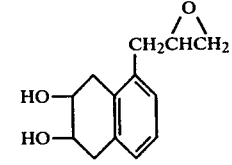
Procedure 60
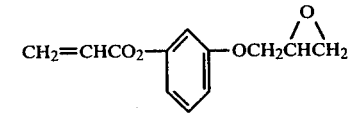
Procedure 62
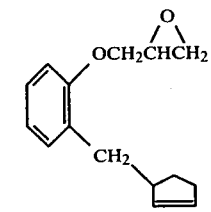
Procedure 64
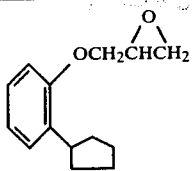
Procedure 53
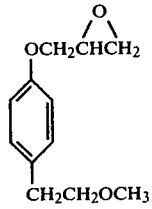
Procedure 55
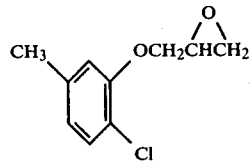
Procedure 57
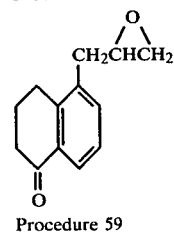
Procedure 59
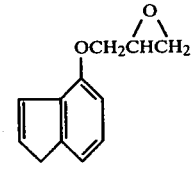
Procedure 61
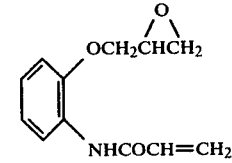
Procedure 63
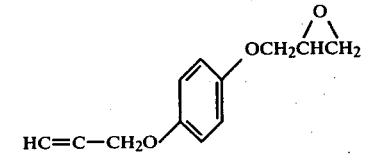
Procedure 65
*Physical properties are reported below.

Procedure 19.
1-[[2-(3-INDOLYL)-1,1-DIMETHYLETHYL]AMINO]-3-[2-(2-PROPENYL)PHENOXY]-2-PROPANOL HYDROCHLORIDE M.p. 163.0°–168.5° (corr.), recrystallized from MeOH/i-Pr$_2$O.

Anal. Found: C, 69.22; H, 7.56; N, 6.70.

NMR (DMSO-d$_6$): 1.30 (6,s); 3.32 (6,m); 4.20 (3,m); 5.03 (2,m); 6.00 (2,m); 7.25 (9,m); 8.90 (1,bs); 9.60 (1,bs); and 11.40 (1,bs).

IR: 752, 1120, 1245, 1455, 1490, 1590, 1600, 2790, 2980, and 3350.

Procedure 22.
1-[[2-(3-INDOLYL)-1,1-DIMETHYLETHYL]AMINO]-3-PHENOXY-2-PROPANOL HYDROCHLORIDE M.p. 176°–177° C. (corr.), recrystallized from CH$_3$CN.

Anal. Found: C, 67.34; H, 7.23; N, 7.66.

NMR (DMSO-d$_6$): 1.36 (6,s); 3.21 (4,m,); 4.20 (3,m); 5.90 (1,bs); 7.29 (10, m,): 9.00 (1,bs); 9.51 (1,bs).

IR: 750, 1245, 1460, 1500, 1590, 1600, 2800, 2980, and 3300.

Procedure 23.
1-[[2-(3-INDOLYL)-1,1-DIMETHYLETHYL]AMINO]-3-[2-(METHYLTHIO)PHENOXY]-2-PROPANOL OXALATE (2:1) HYDRATE M.p. 195°–197° C. (corr.), recrystallized from MeOH/EtOH.

Anal. Found: C, 63.48; H, 6.70; N, 6.40; H$_2$O, 1.11.

NMR (DMSO-d$_6$): 1.25 (6,s); 2.37 (3,s); 3.16 (4.m.); 4.19 (3.m); 7.24 (12,m+bs); 11.30 (1,bs).

IR: 750, 1240, 1310, 1445, 1480, 1580, 1610, 2800, and 2980.

Procedure 25.
2-[2-HYDROXY-3-[[2-(3-INDOLYL)-1,1-DIMETHYLETHYL]AMINO]PROPOXY]BENZAMIDE ETHYL ACETATE SOLVATE M.p. 66°–75° C. (corr.), recrystallized from EtOAc/(i-Pr)$_2$O.

Anal. Found: C, 67.11; H, 7.44; N, 9.66.

NMR (DMSO-d$_6$): 1.14 (6,s); 2.80 (4,m); 3.70 (2,bs); 4.14 (3,m); 7.30 (11, m+bs); 11.10 (1,bs).

IR: 745, 1240, 1460, 1590, 1600, 2970, and 3420.

Procedure 26A.
2-[2-HYDROXY-3-[[2-(3-INDOLYL)-1,1-DIMETHYLETHYL]AMINO]PROPOXY]BENZONITRILE HYDROCHLORIDE A solution of 2-[(2,3-epoxy)propoxy]benzonitrile (18.3 g., 0.10 mole) and 2-(3-indolyl)-1,1-dimethylethylamine (15.2 g., 0.08 mole), in 500 ml. of abs. EtOH was stirred at reflux overnight. After concentration of the reaction mixture to approximately 200 ml. and seeding, crude product began to precipitate. The mixture was then cooled and the precipitate separated by filtration to give 24.8 g. of the free base form of the product, white solid, m.p. 120°–123°. The crude solid was dissolved in 400 ml. of boiling MeOH, and the solution was cooled with stirring, as a by-product 1,1'-[[1,1-dimethyl-2-(1H-indol-3yl)ethyl]imino]bis[3-(2-cyanophenoxy)-2-propanol] precipitated. The by-product was collected on a filter and air dried to give 2.2 g., m.p. 180°–187°. The MeOH filtrate was then taken to dryness. The residual solid was dissolved in 200 ml. of i-PrOH and acidified with ethanolic HCl. Seeding followed by 18 hours standing in the cold afforded the product as the crystalline hydrochloride. Filtration of the mixture gave 19.8 g., of solid, m.p. 179°–183°. One recrystallization from abs. EtOH gave 15.5 g. (48%) of white solid, m.p. 185°–187°. TLC on silica gel (9CH$_2$Cl$_2$, 10 MeOH, 1NH$_4$OH) showed a single spot (R$_f$=0.5, u.v.).

Anal. Found: C, 65.91; H, 6.64; N, 10.46.

NMR (DMSO-d$_6$): 1.32 (6,s); 3.24 (4,m); 4.32 (3,m); 6.06 (1,bs); 7.38 (9,m); 8.90 (1,bs); 9.32 (1,bs); 11.18 (1,bs).

IR: 750, 1110, 1260, 1290, 1450, 1490, 1580, 1600, 2230, and 2980.

The intermediates employed in Procedure 26A were prepared as described in Procedures 26B and 26C.

Procedure 26B.
2-[(2,3-EPOXY)PROPOXY]BENZONITRILE

A solution of 2-cyanophenol (25.0 g., 0.21 mole), epichlorohydrin (117 g., 1.26 mole), and piperidine (10 drops) was stirred and heated at 115°–120° in an oil bath for 2 hours. The reaction mixture was then concentrated (90°/30 mm) to remove unreacted epichlorohydrin. The residue was diluted with toluene and taken to dryness twice to help remove the last traces of volatile material. The residual oil was dissolved in 263 ml. of THF, and the solution stirred at 40°–50° for 1 hour with 263 ml. of 1 N NaOH. The organic layer was separated and concentrated to give an oil which was combined with the aqueous phase. The mixture was extracted with CH$_2$Cl$_2$, and the extract dried (MgSO$_4$) and concentrated to give 36.6 g (100%) of oil which slowly crystallized to a waxy solid. This product was used without further purification in Procedure 26A.

Procedure 26C.
2-(3-INDOLYL)-1,1-DIMETHYLETHYLAMINE

A mixture of gramine (120.0 g., 0.69 mole), 2-nitropropane (443 ml.), and NaOH (28.8 g., 0.72 mole) was stirred and gradually heated to reflux under N$_2$. After a 6.5 hour reflux period, the reaction mixture was allowed to stand at room temperature overnight, and then diluted with 600 ml. of 10% aqueous AcOH. The mixture was extracted with 1.5 l of Et$_2$O, and the organic layer washed with H$_2$O (4×500 ml.). Concentration of the Et$_2$O solution in vacuum gave an oil which was dissolved in 500 ml. of 95% EtOH. This solution was diluted with 300 ml. of H$_2$O. (Seeding and scratching early in the dilution kept the product from oiling out). After cooling, the yellow solid was collected on a filter to give 105 g. (70%) of nitro intermediate, m.p. 72°–74°. The nitro compound was dissolved in 1.3 l of 95% EtOH, and Raney nickel (70 g., EtOH-washed) and added. The mixture was heated to reflux, and a solution of 85% hydrazine hydrate (116 g., 2.3 mole) in 95% EtOH (110 ml.) was added dropwise at a rate to maintain gentle reflux. The mixture was then heated at reflux for an additional 1.5 hours, cooled, and filtered. Concentration of the filtrate gave crude product as a solid. A solution of the solid in 400 ml. of EtOAC was diluted with 500 ml. of (i-Pr)$_2$O and cooled. The white, cottony solid which separated was collected on a filter to give 91 g., (100%) of product, m.p. 122°–126°. It was used in Procedure 26A without further purification.

Procedure 31.
1-(2,3-DIMETHYLPHENOXY)-3-[[2-(3-INDOLYL)-1,1-DIMETHYLETHYL]AMINO]-2-PROPANOL HYDROCHLORIDE M.p. 173.5°–175.5° C. (corr.), recrystallized from i-PrOH.

Anal. Found: C, 68.38; H, 7.65; N, 6.80.

NMR (DMSO-$d_6$): 1.32 (6,s); 2.14 (3,s); 2.23 (3,s); 3.24 (4,m); 4.05 (2,d, 5.0 Hz); 4.36 (1,m); 5.96 (1,bs); 7.20 (8,m); 8.90 (1,bs); 9.40 (1,bs).

IR: 750, 770, 1110, 1260, 1470, 1580, 2780, 2940, and 3400.

Procedure 32.
1-(4-CHLORO-2-METHYLPHENOXY)-3-[[2-(3-INDOLYL)-1,1-DIMETHYLETHYL]AMINO]-2-PROPANOL OXALATE (2:1) HEHMIHYDRATE M.p. 168°–172° C. (dec.) (corr.), recrystallized from DMF/$H_2O$.

Anal. Found: C, 62.71; H, 6.60; N, 6.43; $H_2O$, 2.58.

NMR (DMSO-$d_6$): 1.18 (6,s); 2.18 (3,s); 3.02 (4,m); 4.05 (3,m); 6.17 (8,m); 7.22 (8,m).

IR: 750, 1250, 1310, 1500, 1600, 1610, 2990, and 3410.

Procedure 35.
1-(2,4-DIMETHYLPHENOXY)-3-[[2-(3-INDOLYL)-1,1-DIMETHYLETHYL]AMINO]-2-PROPANOL HYDROCHLORIDE M.p. 161.5°–164.5° C. (corr.), recrystallized from MeOH/EtOAc.

Anal. Found: C, 68.68; H, 7.77; N, 6.98.

NMR (DMSO-$d_6$): 1.32 (6,s); 2.20 (3,s); 2.21 (3,s); 3.21 (4,m); 4.25 (3,m); 6.05 (1,bs); 7.30 (8,m); 9.00 (2,bs); 11.40 (1,bs).

IR: 750, 1230, 1260, 1460, 1510, 1620, 2940, and 3420.

Procedure 38.
1-[[2-(3-INDOLYL)-1,1-DIMETHYLETHYL]AMINO]-3-[2-METHYL-4-(METHYLSULFONYL)PHENOXY]-2-PROPANOL OXALATE (2:1) HYDRATE M.p. 209.5–211.5 (dec.)(corr.), recrystallized from DMF/abs.EtOH.

Anal. Found: C, 59.39; H, 6.77; N, 5.76; $H_2O$, 2.86.

NMR (DMSO-$d_6$): 1.22 (6,s); 2.26 (3,s); 3.15 (4,m); 3.17 (3.s); 4.21 (3,m); 6.52 (3,bs); 7.30 (8,m); 11.40 (1,bs).

IR: 770, 1135, 1265, 1315, 1500, 1610, 1650, and 3400.

Procedure 43:
1-[[2-(3-INDOLYL)-1,1-DIMETHYLETHYL]AMINO]-3-[2-(1-METHYLPROPYL)PHENOXY]-2-PROPANOL HYDROCHORIDE M.p. 163.0°–166.0° (corr.), recrystallized from MeOH/$CH_3CN$.

Anal. Found: C, 69.34; H, 8.19; N, 6.49.

NMR (DMSO-$d_6$): 0.81 (3,t, 7.0 Hz); 1.17 (3,d, 7.0 Hz); 1.32 (6,s); 1.39 (2,m); 3.28 (5,m); 4.22 (3,m); 6.04 (1,bs); 7.22 (9,m); 9.00 (1,bs); 9.60 (1,bs); 11.20 (1,bs).

IR: 750, 1100, 1240, 1450, 1490, 1582, 1600, 2780, 2960, and 3320.

Procedure 44.
1-(2-CYCLOHEXYLPHENOXY)-3-[[2-(1H-INDOL-3-YL)-1,1-DIMETHYLETHYL]AMINO]-2-PROPANOL HYDROCHLORIDE M.p. 189.5°–191.5° C. (corr.), recrystallized from $CH_3CN$.

Anal. Found: C, 70.73; H, 8.02; N, 6.05.

NMR (DMSO-$d_6$): 1.33 (6,s); 1.73 (10,m); 3.28 (5,m); 4.18 (3,m); 6.10 (1,bs); 7.25 (9,m); 9.00 (1,bs); 9.60 (1,bs); 11.33 (1,bs).

IR: 745, 1230, 1450, 1480, 1580, 1595, 2840, 2920, and 3400.

Procedure 45.
3-(2-ETHYLPHENOXY)-1-[[2-(3-INDOLYL)-1,1-DIMETHYLETHYL]AMINO]-2-PROPANOL HYDROCHLORIDE M.p. 170.0°–171.5° (Corr.) recrystallized from EtOH.

Anal. Found: C, 68.36; H, 7.95; N, 6.85.

NMR: (DMSO-$d_6$): 1.21 (3,5, 7.0 Hz); 1.33 (6.s); 2.64 (2,m); 3.24 (4,m); 4.21 (3,m); 6.00 (1,bs); 7.25 (9,m); 9.00 (1,bs); and 9.55 (1,bs).

IR: 750, 1130, 1240, 1460, 1495, 1590, 1605, 2800, 2970, and 3350.

Procedure 46.
1-(2-FLUOROPHENOXY)-3-[[2-(3-INDOLYL)-1,1-DIMETHYLETHYL]AMINO]-2-PROPANOL OXALATE M.p. 203°–205° C. (dec.) (corr.), recrystallized from DMF/$H_2O$.

Anal. Found: C, 66.10; H, 6.71; N, 7.00.

NMR (DMSO-$d_6$): 1.17 (6,s); 3.00 (4,m); 4.10 (3,m); 5.75 (3,bs); 7.20 (9,m).

IR: 750, 1260, 1315, 1510, 1600, 1620, 2990, and 3400.

Procedure 47:
1-[[2-(3-INDOLYL)-1,1-DIMETHYLETHYL]AMINO]-3-[2-(TRIFLUOROMETHYL)PHENOXY]-2-PROPANOL OXALATE HEMIHYDRATE M.p. 202.5° C. (dec.) (corr.), recrystallized from DMF/abs.EtOH.

Anal. Found: C, 60.10; H, 6.26; N, 6.31; $H_2O$, 1.77.

NMR (DMSO-$d_6$): 1.23 (6,s); 2.79 (2,m); 3.11 (3,m); 4.25 (3,m); 7.33 (11,m); 11.35 (1,bs).

IR: 750, 760, 1120, 1325, 1460, 1500, 1610, 1660, and 2980.

Procedure 48.
1-[[2-(3-INDOLYL)-1,1-DIMETHYLETHYL]AMINO]-3-(2-NITROPHENOXY)-2-PROPANOL M.p. 127°–128° C. (corr.), recrystallized from $CH_3CN$.

Anal. Found: C, 65.87; H, 6.58; N, 10.98.

NMR (DMSO-$d_6$): 1.08 (6,s); 1.60 (1,bs); 2.73 (4,m); 4.02 (3,m); 5.04 (1,bs); 7.32 (9,m); 11.04 (1,bs).

IR: 740, 1270, 1340, 1520, 1600, 2920, 2960, 3240 and 3400.

Procedure 49.
1-(2-AMINOPHENOXY)-3-[[2-(3-INDOLYL)-1,1-DIMETHYLETHYL]AMINO]-2-PROPANOL DIHYDROCHLORIDE M.p. 253.5°–255.5° C. (dec.) (corr.), recrystallized from MeOH/$H_2O$/EtOAc.

Anal. Found: C, 58.92; H, 6.79; N, 9.79.

NMR ($CF_3COOH$); 1.67 (6,s); 3.34 (2,s); 3.67 (2,m); 4.52 (3,m); 7.40 (11, m+bs); 8.90 (2, bs).

IR: 750, 760, 1265, 1460, 1500, 1630, 2600, and 2820.

Procedure 66A.
1-[[2-(1-METHYL-3-INDOLYL)-1,1-DIMETHYLE-THYL]AMINO]-3-(2-METHYLPHENOXY)-2-PROPANOL HYDROCHLORIDE (2-Methylphenoxymethyl)oxirane 4.37 g. (0.027 mole) and α,α-1-trimethyl-1H-dinol-3-yl-ethanamine 5.11 g. (0.025 mole) are mixed and heated at 140° for 30 min. to give the desired product; m.p. 189.5°–192.5° (corr.), after recrystallization from abs. EtOH.

Anal. Found: C, 68.40; H, 7.50; N, 6.86.

NMR (DMSO-d$_6$): 1.32 (6,s); 2.22 (3,s); 3.28 (4,m); 3.79 (3,s); 4.30 (3,m); 5.65 (1,bs); 7.22 (9,m); 9.30 (2,bs).

IR: 745, 1120, 1250, 1380, 1475, 1500, 1590, 1600, 2800, and 2950.

The intermediate amine is prepared as follows.

Procedure 66B.
α,α-1-TRIMETHYL-1H-INDOL-3-ETHANAMINE

Seven grams (0.106 mole) of 85% KOH was ground in a mortar and quickly transferred to a N$_2$-flushed 25 ml. Erlenmeyer flask. DMSO (55 ml.) was added and the mixture was stirred 5 min. Additions of 2-(3-indolyl)-1,1-dimethylethylamine (5 g., 0.27 mole) and iodomethane (3.78 g., 0.027 mole) were each followed by 45 min. stirring, after which the suspension was quenched in 300 ml. of water. Extraction of the mixture with EtOAc, followed by washing of the extracts with water and brine afforded a clear solution which was dried over anh. MgSO$_4$ and evaporated in vacuo (20 mm) to give 5 g., of yellow oil. The hydrochloride salt crystallized from i-PrOH-EtOAc, m.p. 138°–148° (prior shrinking). The free base was used in Procedure 66A without further purification.

Procedure 67A.
2-[2-HYDROXY-3-[[2-(2-METHYL-1H-INDOL-3-YL)-1,1-DIMETHYLETHYL]AMINO]PROPOXY]-BENZONITRILE OXALATE (2:1)

The method of Procedure 4 was applied to the reaction of 10.1 g (0.05 mole) of 2-(2-methyl-3-indolyl)-1,1-dimethylethyl amine and 12.3 g (0.07 mole) of 2-[2,3-epoxy)propoxy]benzonitrile for the production of the desired product. It was purified by column chromatography and silica gel employing 9:1 CHCl$_3$:MeOH for elution as the free base. The free base was an oil which was dissolved in warm isopropanol and acidified with oxalic acid resulting in precipitation of the oxalate (2:1) salt m.p., 218°–221°.

Anal. Found: C, 68.12; H, 6.74; N, 9.76.

NMR (DMSO-d$_6$): 1.18 (6,s); 2.35 (3,s); 3.01 (4,m); 4.20 (3,m); 7.22 (8,m); 7.55 (3,bs); 10.85 (1,bs).

IR: 750, 1290, 1450, 1460, 1490, 1580, and 1600.

Procedure 67B. 2-METHYLGRAMINE

AcOH, 236 ml., was mixed with cooling and stirring with 62 m. of 37% formaldehyde at 10°, and 154 ml of 25% aqueous dimethylamine was added dropwise with cooling so as to maintain the temperature at 10°. A solution of 100 g of 2-methylindole in 160 ml of dioxane was then added dropwise with cooling, again maintaining the temperature at 10°. The mixture was stirred at ice temperature for 1 hour and then overnight at room temperature. The mixture was then poured into 2.0 of water with stirring. A small amount of insoluble material was removed by filtration. The filtrate was treated with activated charcoal, filtered again, and the filtrate cooled and basified by the dropwise addition of about 225 ml. of 50% aqueous sodium hydroxide. The product was collected by filtration, washed with water, and air dried, yield 96 g. This material was dissolved in 700 ml of dilute aqueous HCl, treated with activated carbon, filtered, and again basified after diluting to 2 l. with water. The product was collected, air dried, and recrystallized from acetonitrile, yield 72 g., m.p. 117°–119°.

Procedure 67C.
2-METHYL-3-(2-METHYL-2-NITROPROPYL)-INDOLE

A mixture of 15.0 g (0.069 mole) of 2-methylgramine, 44.0 g. (0.49 mole) of 2-nitropropane, and 2.9 g (0.072 mole) of sodium hydroxide pellets is prepared and heated at reflux for 18 hours. This is allowed to cool to room temperature, and 60 ml of 10% aqueous acetic acid is added. Stirring at room temperature is continued for 1 hr. and the mixture is then diluted with about 150 ml of ether. The ether layer is removed and washed with 3 portions of water. The ether solution is then dried over magnesium sulfate, and the solvent removed by distillation yielding 16.5 g of dark oil which crystallized on standing; recrystallized from EtOH-H$_2$O, yield 12.6 g., m.p. 101°–103°.

Procedure 67D.
α,α-2-TRIMETHYL-1H-INDOL-3-YL-ETHANAMINE

The nitro compound produced in Procedure 67C, 0.6 g (0.054 mole) was dissolved in 150 ml of 95% aqueous ethanol, 8.0 g of activated Raney nickel catalyst was added. The mixture was then heated to boiling and a solution of 13.1 g of 85% hydrazine hydrate in 13 ml of ethanol was added dropwise. The mixture was refluxed for 2 hrs., and the treatment with Raney nickel and hydrazine hydrate was repeated with fresh portions thereof. The mixture was refluxed for 1 hr., and then filtered. The solvent was removed from the filtrate by distillation, and the residual oil became crystalline on standing. This was dissolved in aqueous HCl and washed with 3 portions of methylene chloride. The aqueous layer was then treated with activated charcoal, filtered, and basified with 4 N sodium hydroxide. The product which separated was recovered by extraction with 3 portions of methylene chloride, evaporation of the solvent, and crystallization from isopropyl ether, yield 5.7 g., m.p. 99°–107°.

Procedure 68.
1-[[1,1-DIMETHYL-2-(2-METHYL-3-INDOLYL)-ETHYL]AMINO]-3-(2-METHYLPHENOXY)-2-PROPANOL OXALATE (2:1) HYDRATE α,α-2-trimethyl-1H-indole-3-yl-ethaneamine (Procedure 67D), 5.7 g. (0.028 mole), and 5.1 g. (0.031 mole) of (2-methylphenoxy methyl) oxirane are combined and heated with stirring at 140° for 1 hr. Additional oxirane reactant was then added and heating was continued until TLC revealed that all of the ethaneamine starting material had been consumed. The mixture was then diluted with absolute EtOH and allowed to stand at room temperature overnight. A solution of 3.2 g of oxalic acid dihydrate and absolute ethanol was then added and, after crystallization, the product was collected, yield 7.4 g., m.p. 202°–203° (dec.). The product was recrystallized from DMF-EtOH and dried in vacuo at 100°, yield 5.6 g., m.p. 212.0°–214.0° (dec.) (corr.).

Anal. Found: C, 69.02; H, 7.56; N, 6.83; H$_2$O, 0.96.

NMR (DMSO-d$_6$): 1.16 (6,s); 2.19 (3,s); 2.34 (3,s); 2.98 (4,m); 4.07 (3,m); 6.68 (3,bs); 7.10 (8.m); 10.89 (1,bs).

IR: 750, 1250, 1310, 1460, 1500, 1600, 1610, 2980, and 3400.

Procedure 69A.
2-[2-HYDROXY-3-[[2-(5-METHOXY-1H-INDOL-3-YL)-1,1-DIMETHYLETHYL]AMINO]PROPOXY]-BENZONITRILE HYDROCHLORIDE A mixture of 4.4 g. (0.025 mole) of 2-[(2,3-epoxy)propoxy]benzonitrile and 5.4 g. (0.025 mole) of α,α-dimethyl-5-methoxy-1H-indol-3-yl-ethaneamine was melted with stirring at 120°–130° for 1 hr. The mixture was then cooled, triturated with 250 ml. of EtOAc, and acidified with 5 N ethanolic HCl to pH 2. Unreacted starting material weighing 3 g. was removed as a brown, tacky solid by filtration. On standing overnight, the desired product separated from the filtrate as a white crystalline solid which was collected in 3 crops, all exhibiting R$_f$0.3 by TLC on silica gel employing 9:1 CHCl$_3$: MeOH containing ammonia. This material was recrystallized from MEK:EtOH(20:1), yield 6.1 g, m.p. 1604°–166°.

Anal. Found: C, 64.14; H, 6.54; N, 9.68.

NMR (DMSO-d$_6$9: 1.33 (6,s); 3.18 (4.m); 3.79 (3,s); 4.31 (3,m); 6.06 (1,d, 4.8 Hz); 7.20 (8,m); 8.85 (1,bs); 9.35 (1,bs); 11.00 (1,bs).

IR: 760, 1260, 1290, 1450, 4190, 1580, 1600, 1620, 2220, and 3400.

Procedure 69B: 5-METHOXYGRAMINE

This material was prepared from 5-methoxyindole, formaldehyde, and dimethylamine by reaction thereof in dioxan/aqueous acetic acid according to the method of Procedure 67B. From 58.7 g. of 5-methoxyindole, 40 g. of crude 5-methoxygramine was obtained which was recrystallized from 200 ml. of i-Pr$_2$O, yield, 29.7 g., m.p. 118°–122°. Identity was confirmed by inspection of its NMR spectrum.

Procedure 69C.
5-METHOXY-3-(2-METHYL-2-NITROPROPYL)INDOLE

This material was prepared by the reaction of 5-methoxygramine (Procedure 69B) and 2-nitropropane substantially as described in Procedure 67C. The product was initially recovered as a dark oil which crystallized from i-Pr$_2$O solution after treatment thereof with activated carbon, yield 31.3 g. (from 33 g. of 5-methoxygramine), m.p. 83°–85°. The identity of the product was confirmed by inspection of its NMR spectrum.

Procedure 69D.
5-METHOXY-α,α-DIMETHYL-1H-INDOL-3-YL-ETHANEAMINE

The nitro compound produced in Procedure 69C was reduced with Raney nickel and hydrazine hydrate according to the method of Procedure 67D. The structure of the product was confirmed by examination of the NMR spectrum, m.p. 114°–116°, yield 25.8 g. from 31.3 g. of nitro compound.

Procedure 70.
1-[[2-(5-METHOXY-3-INDOLYL)-1,1-DIMETHYLETHYL]AMINO]-3-(2-METHYLPHENOXY)-2-PROPANOL HYDROCHLORIDE (2-Methylphenoxymethyl)oxirane, 4.1 g., (0.025 mole) and 5.4 g. (0.025 mole) of 5-methoxy-α,α-dimethyl-1H-indol-3-yl-ethaneamine were mixed and heated at 130° for 2 hrs. The mixture was allowed to cool, but while still warm was dissolved in 60 ml. of acetonitrile and acidified with ethanolic 5 N HCl to pH 2. Th product crystallized as the hydrochloride salt, yield 8.3 g.; recrystallized from isopropanol/methanol, yield 7.4 g., m.p. 201.0°–203.0°.

Anal. Found: C, 65.93; H, 7.20 N, 6.61.

NMR (DMSO-d$_6$): 1.32 (6,s); 2.21 (3,s); 3.20 (4,m); 3.79 (3,s); 7.04 (2,m); 4.36 (1,m); 5.95 (1,bs); 7.05 (8,m); 8.90 (2,bs).

IR: 750, 1250, 1440, 1460, 1500, 1590, 1630 and 2940.

Procedure 71A.
1-[[2-(5-BROMO-3-INDOLYL)-1,1-DIMETHYLETHYL]AMINO]-3-(2-METHYLPHENOXY)-2-PROPANOL HYDROCHLORIDE (2-Methylphenoxymethyl)oxirane, 4.1 g. (0.025 mole) and 6.65 g. (0.025 mole) of 5-bromo-α,α-dimethyl-1H-indol-3-yl-ethaneamine were mixed and heated at 140° for 1 hr. The mixture was then cooled and dissolved in 40 ml. of acetonitrile while still warm. The product was converted to the hydrochloride salt by treatment of the solution with 5 N ethanolic HCl. The solvent was removed by distillation and the residue dissolved in 30 ml. of acetonitrile. The product crystallized from this solution, yield 11.0 g., m.p. 197°–199°. This material was recrystallized from methanol/isopropanol, yield 8.0 g., m.p. 198.0°–200.0° dec. (corr.).

Anal. Found: C, 56.10; H, 6.25; N, 5.79.

NMR (DMSO-d$_6$): 1.30 (6,s); 2.20 (3,s); 3.19 (4,m); 4.07 (2,m); 4.36 (1,m); 5.30 (1,bs); 7.11 (7,m); 7.86 (1,m); 8.80 (1,bs).

IR: 760, 1250, 1470, 1500, 1590, 1610, 2800, 2980, and 3400.

Procedure 71B. 5-BROMOGRAMINE

This material was prepared by the method of Procedure 67B from 49.5 g. of 5-bromoindole, 20 ml. of 37% aqueous formaldehyde, 55 ml. of 25% aqueous dimethylamine, 250 ml. of acetic acid and 250 ml. of dioxane; yield 60.6 g., m.p. 154°–156° C. The structure was confirmed by examination of the NMR spectrum.

Procedure 71C.
5-BROMO-3-(2-METHYL-2-NITROPROPYL)INDOLE

5-Bromogramine, 60.0 g., 165 g. of 2-nitropropane, and 10.5 g. of sodium hydroxide pellets were caused to react under the conditions of Procedure 67C. The product was recovered as a dark syrup-like liquid from which the crystalline product was obtained by dissolving in IPr$_2$O. The crystalline material was recrystallized from IPr$_2$O to yield 48.6 g. of tan crystalline product, m.p. 106°–109°. The structure was confirmed by examination of the NMR spectrum.

Procedure 71D.
5-BROMO-α,α-DIMETHYL-1H-INDOL-3-YL-ETHANEAMINE

5-Bromo-3-(2-methyl-2-nitropropyl)indole, 5.9 g. was reduced with Raney nichel and hydrazine hydrate according to the method of Procedure 67D. The crude product was purified by dissolving in 200 ml. of dilute hydrochloric acid, treatment with activated charcoal, filtering, and basification of the filtrate with 10% aqueous sodium hydroxide. Yield 3.8 g. of white powder, m.p. 150°–155° C.

BIOLOGICAL EVALUATION

Three biological tests have been used to gauge the effectiveness of a number of the compounds of Formula I as beta-adrenergic blocking vasodilators. They are described in Procedures 72, 73, and 74 and the results shown in the table. Where a dash (-) appears in the table, the test was not completed.

Procedure 72

Beta-blocking potency is estimated in the conscious rat (Test 349F) and is reported as a potency, compared to propranolol, with respect to prevention of the isoproterenol-induced increase in heart rate at 2 and 4 hrs. after oral dosing. The doses of propranolol and test compound necessary to evoke the same blocking effect are determined and the former is divided by the latter to give a relative potency factor.

Procedure 73

The efficacy of antihypertensive agents other than adrenergic $\beta$-receptor blocking agents is commonly estimated in the spontaneous hypertensive rat (Test 410C). Values for blood pressure listed in the table represent changes (positive or negative) in the blood pressure of test animals prior to and 22 hrs. after oral doses of 100 mg/kg of test compounds; the observed percentage change in heart rate is noted as well. A fall in blood pressure in the range of 19-24 mmHg is considered "questionable." "Active" and "inactive" designations are decreases greater and less than that range.

Procedure 74

The angiotensin-maintained ganglion-blocked rat model is utilized as a screening test for estimation of the vasodilator component of activity. Values listed in the table note percentage changes in blood pressure in anesthetized rats 30 min. after intravenous dosing with test compound at 3 mg/kg. Borderline activity is defined as a 15-20% decrease in blood pressure measured 30 min. after dosing. "Active" and "inactive" designations are increases greater and less than that range.

| | Adrenergic $\beta$-Receptor Blocking and Vasodilator Action | | | | |
|---|---|---|---|---|---|
| | $\beta$-Adren- | Antihypertensive | | Vasocli- | |
| Proc. No. | ergic Block[1] | $\Delta$mm Hg[2] | % $\Delta$ H.R.[3] | lator[4] % $\Delta$ b.p. | ALD$_{50}$[5] |
| 3 | 7 | −5 | −29 | — | >2000 |
| 4 | 7 | 0 | −14 | — | 125-250 |
| 5 | 8 | −3 | −23 | — | >2000 |
| 6 | 7 | 0 | −22 | — | >2000 |
| 7 | 7 | 0 | −20 | — | — |
| 8 | 7 | 0 | −21 | — | 250-500 |
| 9 | — | −12 | 0 | — | 500 |
| 10 | 10 | −25 | −12 | −22[6] | 125-250 |
| 11 | | | | | |
| 12 | 7 | −13 | −10 | — | — |
| 13 | — | +6 | +19 | −6 | >2000 |
| 14 | | | | | |
| 19 | ca. 10 | −24 | −25 | +19 | 125 |
| 22 | 2-5 | −5 | −8 | −30 | 500-100 |
| 23 | 5-10 | −12 | −11 | −29 | 250-500 |
| 25 | 2-5 | −35 | −8 | −25 | >1000 |
| 26 | 5 | −44 | −14 | −25 | 125-250 |
| 31 | >10 | −37 | −13 | +8 | >2000 |
| 32 | 1 | −14 | −25 | +11 | >2000 |
| 35 | 10 | −30 | −22 | +13 | 2000 |
| 38 | 2 | −23 | −19 | −8 | >2000 |
| 43 | 5-10 | −24 | −20 | +22 | 500 |
| 44 | 6 | −13 | −23 | +18 | >1200 |
| 45 | 5-10 | −22 | −14 | −27 | 500 |
| 46 | >10 | −19 | −5 | −33 | 500-1000 |
| 47 | 10 | −37 | −3 | −34 | 125 |
| 48 | 2-5 | −22 | −5 | −38 | 125 |
| 49 | 1-3 | −40 | −19 | −11 | 500-1000 |
| 66A | 10 | −21 | −8 | −3 | 250 |
| 67A | 10 | −21 | −9 | −36 | 1000-2000 |
| 68 | 10 | −28 | −4 | −22 | 2000 |
| 69A | 10 | −27 | −17 | −49 | 1000-2000 |
| 70 | 10 | −22 | 0 | −41 | 2000 |
| 71A | 10 | −28 | −4 | −13 | 2000 |

[1] Potency factor relative to propranolol - Procedure 72.
[2] Change in blood pressure - Procedure 73 dose 100 mg/kg p.o.
[3] Percent change in heart rate - Procedure 73, dose 100 mg/kg P.O.
[4] Procedure 74.
[5] Mouse treated orally. Approximate value.
[6] Dose 10 mg/kg I.V.
[7] Adrenergic $\beta$-receptor blocking action was demonstrated in vitro using tracheal and atrial tissue.
[8] Adrenergic $\beta$-receptor blocking action could not be demonstrated in vitro.

Procedure 75.
2-[2-HYDROXY-3-[[2-(3-INDOLYL)-1,1-DIMETHYLETHYL]AMINO]PROPOXY]BENZONITRILE The crude free base produced as a white solid, m.p. 120°-123° in Procedure 26A, 3.0 g., was dissolved in abs. ethanol, treted with decolorizing charcoal, and filtered. The pure free base crystallized from the filtrate and was collected and air dried, weight 1.6 g., m.p. 125°-127°.

Anal. Found: C, 72.58; H, 7.09; N, 11.58.

NMR (DMSO-d$_6$): 1.02 (6,s); 1.50 (1,bs); 2.74 (4,m); 4.02 (3,m); 4.98 (1,bs); 7.35 (9 ,m); and 10.80 (1,bs).

IR: 745, 1260, 1290, 1440, 1490, 1580, 1600, 2220, 2960, and 3400.

Procedure 76-82. VARIOUS SALTS OF 2-[2-HYDROXY-3-[[2-(3-INDOLYL)-1,1-DIMETHYLETHYL]AMINO]PROPOXY]BENZONITRILE The salts listed in the following table were prepared by dissolving one molecular proportion of the free base prepared in Procedure 75 in ethanol, and treating with the acid shown in the table in the proportion stated. In most instances, the salt crystallized from the reaction solution without evaporation of the solvent. The salt was collected and recrystallized. The melting points, formulas, and the recrystallization solvents in each instance are listed in the table. The formula was determined by elemental analysis. The NMR and IR spectra were examined in each instance and found to confirm the structure and formula assigned.

| | | Procedures 76-82 | | | |
|---|---|---|---|---|---|
| Proc. No | Acid | Proportion[1] | Recryst. Solvent | m.p.° | Formula | ALD$_{50}$[3] |
| 76 | Succinic | 0.5 | EtOH | 156-157 | $C_{22}H_{25}N_3O_2 \cdot \frac{1}{2}C_4H_6O_4$ | 248 |

-continued

Procedures 76–82

| Proc. No | Acid | Proportion[1] | Recryst. Solvent | m.p.° | Formula | ALD$_{50}$[3] |
|---|---|---|---|---|---|---|
| 77 | Malic | 1.0 | MeOH | 190–192 | $C_{22}H_{25}N_3O_2 \cdot \frac{1}{2}C_4H_6O_5 \cdot \frac{1}{2}H_2O$ | 310 |
| 78 | Mucic | 0.5 | DMF/EtOH[2] | 174–176 (dec.) | $C_{22}H_{25}N_3O_2 \cdot \frac{1}{2}C_6H_{10}O_8 \cdot \frac{1}{2}H_2O$ | 260 |
| 79 | Fumaric | 0.5 | abs. EtOH/MeOH | 150–158 | $C_{22}H_{25}N_3O_2 \cdot \frac{1}{2}C_4H_4O_4 \cdot \frac{1}{2}H_2O$ | 270 |
| 80 | Mandelic | 1.0 | EtOH | 129–131 | $C_{22}H_{25}N_3O_2 \cdot C_8H_8O_3$ | 255 |
| 81 | Malonic | 1.0 | EtOH | 172–173 (dec.) | $C_{22}H_{25}N_3O_2 \cdot \frac{1}{2}C_3H_4O_4$ | 210 |
| 82 | Oxalic |  |  | 238.5–243.0 (dec.) | $C_{22}H_{25}N_3O_2 \cdot \frac{1}{2}C_2H_2O_4 \cdot \frac{1}{2}H_2O$ | 2000 |

[1]Moles of acid per mole of base.
[2]MeOH used as reaction solvent.
[3]Mouse treated orally; approximate value.

What is claimed is:

1. A compound having the formula

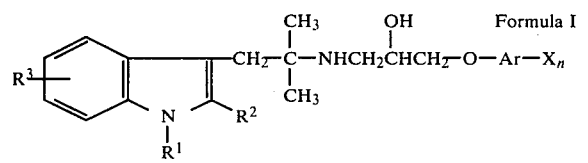

Formula I and the acid addition salts thereof wherein one of
$R^1$ and $R^2$ is hydrogen and the other is hydrogen or alkyl having 1 to 4 carbon atoms,
$R^3$ is H, halogen, alkyl having 1 to 4 carbon atoms, or alkoxy having 1 to 4 carbon atoms and is located in the 4-, 5-, 6-, or 7- positions of the indole ring,
Ar is selected from the group consisting of phenyl and naphthyl,
X refers to 1 or 2 optional sterically compatible Ar-attached substituents which are independently selected from the group consisting of alkyl, alkenyl, alkynyl, alkoxy, alkenoxy, alkynoxy, alkoxyalkyl, alkanoyl, alkenoyl, alkanoyloxy, alkenoyloxy, alkylsulfonyl, alkylsulfinyl, alkylthio, alkanoylamino, alkenoylamino, alkoxycarbonyl, alkenoxycarbonyl, alkoxycarbonylamino, alkoxycarbonylaminoalkyl, cycloalkyl having 3 to 6 ring members and 1 to 3 optional alkyl substituents, cycloalkenyl having 4 to 6 ring members and up to 3 optional alkyl substituents, cycloalkylalkyl having 3 to 6 ring members and up to 3 optional alkyl substituents, cycloalkenylalkyl having 4 to 6 ring members and up to 3 optional alkyl substituents with the additional proviso that each of the foregoing Ar-attached substituents has up to 8 carbon atoms, trifluoromethyl, nitro, amino, hydroxyl, halogen, aminocarbonyl, cyano, cyanoalkyl having from 2 to 4 carbon atoms, aminocarbonylalkyl having 2 to 4 carbon atoms,
n is the integer 0, 1, or 2 signifying the number of X groups, or
Ar-$X_n$ as a unit refers to 4-indenyl, 6,7-dihydroxy-5,6,7,8-tetrahydro-1-napthyl, or 5-oxo-5,6,7,8-tetrahydro-1-naphthyl.

2. The compound of claim 1 wherein Ar is phenyl, X is in the ortho-position, and n is the integer 1.

3. The compound of claim 1 wherein Ar is phenyl, X is alkyl having up to 8 carbon atoms, and n is the integer 1.

4. The compound of claim 3 wherein X is methyl.

5. The compound of claim 3, 1-[[2-(3-indolyl)-1,1-dimethylethyl]amino]-3-(2-methylphenoxy)-2-propanol.

6. The compound of claim 3, 1-8 [2-(3-indolyl)-1,1-dimethylethyl]amino]-3-(2-methylphenoxy)-2-propanol hydrochloride.

7. The compound of claim 3, 1-[[2-(3-indolyl)-1,1-dimethylethyl]amino]-3-(3-methylphenoxy)-2-propanol.

8. The compound of claim 3, 1-[[2-(3-indolyl)-1,1-dimethylethyl]amino]-3-(3-methylphenoxy)-2-propanol hydrochloride.

9. The compound of claim 3 wherein X is ethyl.

10. The compound of claim 3, 3-(2-ethylphenoxy)-1-[[2-(3-indolyl)-1,1-dimethylethyl]amino]-2-propanol.

11. The compound of claim 3, 3-(2-ethylphenoxy)-1-[[2-(3-indolyl)-1,1-dimethylethyl]amino]-2-propanol hydrochloride.

12. The compound of claim 3 wherein X is butyl.

13. The compound of claim 3, 1-[[2-(3-indolyl)-1,1-dimethylethyl]amino]-3-[2-(2-methyl-1-propyl)phenoxy]-2-propanol.

14. The compound of claim 3, 1-[[2-(3-indolyl)-1,1-dimethylethyl]amino]-3-[2-(2-methyl-1-propyl)phenoxy]-2-propanol hydrochloride.

15. The compound of claim 3, 1-[[1,1-dimethyl-2-(2-methyl-3-indolyl)ethyl]amino]-3-(2-methylphenoxy)-2-propanol.

16. The compound of claim 3, 1-[[2-(1-methyl-3-indolyl)-1,1-dimethylethyl]amino]-3-(2-methylphenoxy)-2-propanol.

17. The compound of claim 3, 1-[[2-(1-methyl-3-indolyl)-1,1-dimethylethyl]amino]-3-(2-methylphenoxy)-2-propanol hydrochloride.

18. The compound of claim 3, 1-[[2-(5-bromo-3-indolyl)-1,1-dimethylethyl]amino]-3-(2-methylphenoxy)-2-propanol.

19. The compound of claim 3, 1-[[2-(5-bromo-3-indolyl)-1,1-dimethylethyl]amino]-3-(2-methylphenoxy)-2-propanol hydrochloride.

20. The compound of claim 3, 1-[[2-(5-methoxy-3-indolyl)-1,1-dimethylethyl]amino]-3-(2-methylphenoxy)-2-propanol.

21. The compound of claim 3, 1-[[2-(5-methoxy-3-indolyl)-1,1-dimethylethyl]amino]-3-(2-methylphenoxy)-2-propanol hydrochloride.

22. The compound of claim 1 wherein Ar is phenyl, X is halogen, and n is the integer 1.

23. The compound of claim 22 wherein X is chlorine.

24. The compound of claim 22, 1-(2-chlorophenoxy)-3-[[2-(3-indolyl)-1,1-dimethylethyl]amino]-2-propanol.

25. The compound of claim 22, 1-(2-chlorophenoxy)-3-[[2-(3-indolyl)-1,1-dimethylethyl]amino]-2-propanol hydrochloride.

26. The compound of claim 22, 1-(3-chlorophenoxy)-3-[[2-(3-indolyl)-1,1-dimethylethyl]amino]-2-propanol.

27. The compound of claim 22, 1-(3-chlorophenoxy)-3-[[2-(3-indolyl)-1,1-dimethylethyl]amino]-2-propanol hydrochloride.

28. The compound of claim 22 wherein X is fluorine.

29. The compound of claim 22, 1-(2-fluorophenoxy)-3-[[2-(3-indolyl)-1,1-dimethylethyl]amino]-2-propanol.

30. The compound of claim 1 wherein Ar is phenyl, X is alkynyl having up to 8 carbon atoms, and n is the integer 1.

31. The compound of claim 30 wherein X is ethynyl.

32. The compound of claim 1 wherein Ar is phenyl, X is lower alkoxy having up to 8 carbon atoms, and n is the integer 1.

33. The compound of claim 32 wherein X is ethoxy.

34. The compound of claim 32, 1-(2-ethoxyphenoxy)-3-[[2-(3-indolyl)-1,1-dimethylethyl]amino]-2-propanol.

35. The compound of claim 32, 1-(2-ethoxyphenoxy)-3-[[2-(3-indolyl)-1,1-dimethylethyl]amino]-2-propanol hydrochloride.

36. The compound of claim 1 wherein Ar is phenyl, X is lower alkylsulfonyl having up to 8 carbon atoms, and n is the integer 1.

37. The compound of claim 36, 1-[[2-(3-indolyl)-1,1-dimethylethyl]amino]-3-(4-methylsulfonyl)phenoxy-2-propanol.

38. The compound of claim 36, 1-[[2-(3-indolyl)-1,1-dimethylethyl]amino]-3-(4-methylsulfonyl)phenoxy-2-propanol hydrochloride.

39. The compound of claim 36, 1-[[2-(3-indolyl)-1,1-dimethylethyl]amino]-3-(2-methylsulfonyl)phenoxy-2-propanol.

40. The compound of claim 36, 1-[[2-(3-indolyl)-1,1-dimethylethyl]amino]-3-(2-methylsulfonyl)phenoxy-2-propanol hydrochloride.

41. The compound of claim 1 wherein Ar is phenyl, X is alkylsulfonyl or alkyl each having up to 8 carbon atoms, and n is the integer 2.

42. The compound of claim 41, 1-[[2-(3-indolyl)-1,1-dimethylethyl]amino]-3-[4-(methylsulfonyl)-m-tolyloxy]-2-propanol.

43. The compound of claim 41, 1-[[2-(3-indolyl)-1,1-dimethylethyl]amino]-3-[4-methylsulfonyl)-m-tolyloxy]-2-propanol hydrochloride.

44. The compound of claim 41, 1-[[2-(3-indolyl)-1,1-dimethylethyl]amino]-3-[2-methyl-4-(methylsulfonyl)phenoxy]-2-propanol.

45. The compound of claim 1, 1-[[2-(3-indolyl)-1,1-dimethylethyl]amino]-3-(1-naphthyloxy)-2-propanol.

46. The compound of claim 1, 1-[[2-(3-indolyl)-1,1-dimethylethyl]amino]-3-(1-naphthyloxy)-2-propanol hydrochloride.

47. The compound of claim 1 wherein Ar is phenyl, X is alkanoyl having up to 8 carbon atoms, and n is the integer 1.

48. The compound of claim 47, 1-(2-acetylphenoxy)-3-[[2-(3-indolyl)-1,1-dimethylethyl]amino]-2-propanol.

49. The compound of claim 47, 1-(2-acetylphenoxy)-3-[[2-(3-indolyl)-1,1-dimethylethyl]amino]-2-propanol hydrochloride.

50. The compound of claim 1 wherein Ar is phenyl, X is alkenyl having up to 8 carbon atoms, and n is the integer 1.

51. The compound of claim 50, 1-[[2-(3-indolyl)-1,1-dimethylethyl]amino]-3-[2-(2-propenyl)phenoxy]-2-propanol.

52. The compound of claim 50, 1-[[2-(3-indolyl)-1,1-dimethylethyl]amino]-3-[2-(2-propenyl)phenoxy]-2-propanol hydrochloride.

53. The compound of claim 1 wherein Ar is phenyl, X is alkylsulfinyl having up to 8 carbon atoms, and n is the integer 1.

54. The compound of claim 1 wherein Ar is phenyl, X is lower alkylthio having up to 8 carbon atoms, and n is the integer 1.

55. The compound of claim 54, 1-[[2-(3-indolyl)-1,1-dimethylethyl]amino]-3-[2-(methylthio)phenoxy]-2-propanol.

56. The compound of claim 1 wherein Ar is phenyl, X is cyano, and n is the integer 1.

57. The compound of claim 56, 2-[2-hydroxy-3-[[2-(3-indolyl)-1,1-dimethylethyl]amino]propoxy]benzonitrile, or a pharmaceutically acceptable acid addition salt thereof.

58. The compound of claim 56, 2-[2-hydroxy-3-[[2-(3-indolyl)-1,1-dimethylethyl]amino]propoxy]benzonitrile.

59. The compound of claim 56, 2-[2-hydroxy-3-[[2-(3-indolyl)-1,1-dimethylethyl]amino]propoxy]benzonitrile hydrochloride.

60. The compound of claim 56, 2-[2-hydroxy-3-[[2-(3-indolyl)-1,1-dimethylethyl]amino]propoxy]benzonitrile succinate.

61. The compound of claim 56, 2-[2-hydroxy-3-[[2-(3-indolyl)-1,1-dimethylethyl]amino]propoxy]benzonitrile malate.

62. The compound of claim 56, 2-[2-hydroxy-3-[[2-(3-indolyl)-1,1-dimethylethyl]amino]propoxy]benzonitrile mucate.

63. The compound of claim 56, 2-[2-hydroxy-3-[[2-(3-indolyl)-1,1-dimethylethyl]amino]propoxy]benzonitrile fumarate.

64. The compound of claim 56, 2-[2-hydroxy-3-[[2-(3-indolyl)-1,1-dimethylethyl]amino]propoxy]benzonitrile mandelate.

65. The compound of claim 56, 2-[2-hydroxy-3-[[2-(3-indolyl)-1,1-dimethylethyl]amino]propoxy]benzonitrile malonate.

66. The compound of claim 56, 2-[2-hydroxy-3-[[2-(2-methyl-1$\underline{H}$-indol-3-yl)-1,1-dimethylethyl]amino]propoxy]benzonitrile.

67. The compound of claim 56, 2-[2-hydroxy-3-[[2-(5-methoxy-1$\underline{H}$-indol-3-yl)-1,1-dimethylethyl]amino]propoxy]benzonitrile.

68. The compound of claim 56, 2-[2-hydroxy-3-[[2-(5-methoxy-1$\underline{H}$-indol-3-yl)-1,1-dimethylethyl]amino]propoxy]benzonitrile hydrochloride.

69. The compound of claim 1 wherein Ar is phenyl, X is cyanoalkyl having from 2 to 4 carbon atoms, and n is the integer 1.

70. The compound of claim 1 wherein Ar is phenyl, X is alkenoxy having up to 8 carbon atoms, and n is the integer 1.

71. The compound of claim 1 wherein Ar is phenyl, X is alkenoyl having up to 8 carbon atoms, and n is the integer 1.

72. The compound of claim 1 having Formula I wherein Ar is phenyl, X is alkoxy having up to 8 carbon atoms, and n is the integer 2.

73. The compound of claim 1 having Formula I wherein Ar is phenyl, X is alkyl having up to 8 carbon atoms, and n is the integer 2.

74. The compound of claim 73, 1-(2,3-dimethylphenoxy)-3-[[2-(3-indolyl)-1,1-dimethylethyl]amino]-2-propanol.

75. The compound of claim 73, 1-(2,3-dimethylphenoxy)-3-[[2-(3-indolyl)-1,1-dimethylethyl]amino]-2-propanol hydrochloride.

76. The compound of claim 73, 1-(2,4-dimethylphenoxy)-3-[[2-(3-indolyl)-1,1-dimethylethyl]amino]-2-propanol.

77. The compound of claim 73, 1-(2,4-dimethylphenoxy)-3-[[2-(3-indolyl)-1,1-dimethylethyl]amino]-2-propanol hydrochloride.

78. The compound of claim 73, 1-(2,6-dimethylphenoxy)-3-[[2-(3-indolyl)-1,1-dimethylethyl]amino]-2-propanol.

79. The compound of claim 73, 1-(2,6-dimethylphenoxy)-3-[[2-(3-indolyl)-1,1-dimethylethyl]amino]-2-propanol hydrochloride.

80. The compound of claim 1 wherein Ar is phenyl, X is cycloalkyl having up to 8 carbon atoms including 3 to 6 ring members and from 1 to 3 optional alkyl substituents, and n is the integer 1.

81. The compound of claim 80, 1-(2-cyclohexylphenoxy)-3-[[2-(1H-indol-3-yl)-1,1-dimethylethyl]amino]-2-propanol.

82. The compound of claim 80, 1-(2-cyclohexylphenoxy)-3-[[2-(1H-indol-3-yl)-1,1-dimethylethyl]amino]-2-propanol hydrochloride.

83. The compound of claim 1, 1-[[2-(3-indolyl)-1,1-dimethylethyl]amino]-3-phenoxy-2-propanol.

84. The compound of claim 1, 1-[[2-(3-indolyl)-1,1-dimethylethyl]amino]-3-phenoxy-2-propanol hydrochloride.

85. The compound of claim 1 wherein Ar is phenyl, X is trifluoromethyl, and n is the integer 1.

86. The compound of claim 85, 1-[[2-(3-indolyl)-1,1-dimethylethyl]amino]-3-[2-(trifluoromethyl)phenoxy]-2-propanol.

87. The compound of claim 1 wherein Ar is phenyl, X is aminocarbonyl, and n is the integer 1.

88. The compound of claim 87, 2-[2-hydroxy-3-[[2-(3-indolyl)-1,1-dimethylethyl]amino]propoxy]benzamide.

89. The compound of claim 1, wherein Ar is phenyl, X is nitro, and n is the integer 1.

90. The compound of claim 89, 1-[[2-(3-indolyl)-1,1-dimethylethyl]amino]-3-(2-nitrophenoxy)-2-propanol.

91. The compound of claim 1 wherein Ar is phenyl, X is NH$_2$, and n is the integer 1.

92. The compound of claim 91, 1-(2-aminophenoxy)-3-[[2-(3-indolyl)-1,1-dimethylethyl]amino]-2-propanol.

93. The compound of claim 91, 1-(2-aminophenoxy)-3-[[2-(3-indolyl)-1,1-dimethylethyl]amino]-2-propanol hydrochloride.

94. The compound of claim 1 wherein Ar is phenyl, X is methyl and chloro, and n is the integer 2.

95. The compound of claim 94, 1-(4-chloro-2-methylphenoxy)-3-[[2-(3-indolyl)-1,1-dimethylethyl]amino]-2-propanol.

96. The compound of claim 1 wherein Ar is phenyl, X is cyanomethyl and acetyl, and n is the integer 2.

97. The compound of claim 96, 5-acetyl-2-[3-[[1,1-dimethyl-2-(1H-indol-3-yl)ethyl]amino]-2-hydroxypropoxy]benzeneacetonitrile.

98. The method of inhibiting β-adrenergic activity in a mammalian host having a condition in which therapeutic benefit is derived from inhibition of the β-adrenergic receptors which comprises administering to said host a non-toxic effective adrenergic β-receptor inhibiting dose of a compound as claimed in claim 1.

99. The method of exerting a vasodilating effect in a mammalian host which comprises administering to a mammal having a condition in which therapeutic benefit is derived from vasodilatation, a non-toxic effective vasodilating dose of a compound as claimed in claim 1.

100. The antihypertensive method which comprises administering to a mammalian host having hypertension a non-toxic antihypertensive effective dose of a compound claimed in claim 1.

101. The antihypertensive method which comprises administering to a mammalian host having hypertension a non-toxic antihypertensive effective dose of a compound claimed in claim 2.

102. The compound of claim 1 wherein Ar is phenyl, X is alkynoxy and n is the integer 1.

103. The compound of claim 1 wherein Ar is phenyl, X is alkoxyalkyl, and n is the integer 1.

104. The compound of claim 1 wherein Ar is phenyl, X is alkoxycarbonylaminoalkyl, and n is the integer 1.

105. The compound of claim 1 wherein Ar is phenyl, X is aminocarbonylalkyl, and n is the integer 1.

106. The compound of claim 1 wherein Ar is naphthyl, X is hydroxy, and n is the integer 1.

* * * * *

UNITED STATES PATENT OFFICE
CERTIFICATE OF CORRECTION

Patent No. 4,234,595           Dated November 18, 1980

Inventor(s) William E. Kreighbaum and William T. Comer

It is certified that error appears in the above-identified patent and that said Letters Patent are hereby corrected as shown below:

Column 5, line 68, delete the phrase "urine volume and a decrease in".

Column 6, lines 1 and 2, delete in their entirety.

Signed and Sealed this

Twenty-fourth Day of March 1981

[SEAL]

Attest:

RENE D. TEGTMEYER

Attesting Officer    Acting Commissioner of Patents and Trademarks